United States Patent
Yamamoto

(12) 
(10) Patent No.: US 10,912,496 B2
(45) Date of Patent: Feb. 9, 2021

(54) BODY CHARACTERISTIC MEASURING DEVICE, STORAGE MEDIUM STORING BODY CHARACTERISTIC MEASUREMENT PROGRAM, AND BODY CHARACTERISTIC MEASUREMENT METHOD

(71) Applicant: FUJITSU LIMITED, Kawasaki (JP)

(72) Inventor: Kiyoko Yamamoto, Kobe (JP)

(73) Assignee: FUJITSU LIMITED, Kawasaki (JP)

( * ) Notice: Subject to any disclaimer, the term of this patent is extended or adjusted under 35 U.S.C. 154(b) by 257 days.

(21) Appl. No.: 15/637,364

(22) Filed: Jun. 29, 2017

(65) Prior Publication Data

US 2018/0028095 A1 Feb. 1, 2018

(30) Foreign Application Priority Data

Jul. 29, 2016 (JP) .................. 2016-150660

(51) Int. Cl.
*A61B 5/11* (2006.01)
*A61B 5/00* (2006.01)
(Continued)

(52) U.S. Cl.
CPC .............. *A61B 5/112* (2013.01); *A01K 29/00* (2013.01); *A61B 5/6823* (2013.01);
(Continued)

(58) Field of Classification Search
CPC ..... A61B 5/112; A61B 5/6823; A61B 5/7235; A61B 5/7275; A61B 5/7242;
(Continued)

(56) References Cited

U.S. PATENT DOCUMENTS

| 10,531,137 B1* | 1/2020 | Matak ................... A63F 13/211 |
| 2007/0130893 A1* | 6/2007 | Davies ................. A01K 11/008 54/1 |

(Continued)

FOREIGN PATENT DOCUMENTS

| JP | 2005-80635 | 3/2005 |
| JP | 2010-282456 | 12/2010 |

(Continued)

OTHER PUBLICATIONS

Horse & Hound "Shoulder lameness: direct trauma injuries", May 25, 2011, https://www.horseandhound.co.uk/horse-care/vet-advice/shoulder-lameness-direct-trauma-injuries-307711 (Year: 2011).*

(Continued)

*Primary Examiner* — Matthew Kremer
*Assistant Examiner* — Avery M Foley
(74) *Attorney, Agent, or Firm* — Staas & Halsey, LLP

(57) ABSTRACT

A body characteristic measurement method causing a computer to execute a process, the process includes: determining a gait of a quadruped based on accelerations, acquired from a multi-axis acceleration sensor attached to the chest of the quadruped, in multiple axial directions; and determining, if the determined gait is gallop or canter, an injury risk of the quadruped based on a waveform of a positive half-wave region of acceleration in a movement direction of the quadruped in the case where an increase in the acceleration in the movement direction of the quadruped is defined as positive.

7 Claims, 24 Drawing Sheets

(51) Int. Cl.
*G16H 40/67* (2018.01)
*A01K 29/00* (2006.01)
*G01R 29/00* (2006.01)

(52) U.S. Cl.
CPC .......... *A61B 5/7235* (2013.01); *A61B 5/7275* (2013.01); *G01R 29/00* (2013.01); *G16H 40/67* (2018.01); *A61B 5/7242* (2013.01); *A61B 2503/40* (2013.01); *A61B 2562/0219* (2013.01)

(58) Field of Classification Search
CPC .............. A61B 5/7282; A61B 2503/40; A61B 2562/0219; G16H 40/67; A01K 29/00; G01R 29/00
See application file for complete search history.

(56) References Cited

U.S. PATENT DOCUMENTS

| | | | | |
|---|---|---|---|---|
| 2016/0073614 | A1* | 3/2016 | Lampe | A01L 11/00 600/408 |
| 2016/0135716 | A1 | 5/2016 | Yamamoto et al. | |
| 2016/0165852 | A1* | 6/2016 | Goldfain | A01K 29/005 340/573.3 |

FOREIGN PATENT DOCUMENTS

| | | |
|---|---|---|
| JP | 2015-84943 | 5/2015 |
| JP | 2016-013112 | 1/2016 |
| JP | 2016-96758 | 5/2016 |

OTHER PUBLICATIONS

Extended European Search Report dated Dec. 18, 2017, from European Application No. 17180233.3, 9 pages.

M. Ferrari et al., "The effect of training on stride parameters in a cohort of National Hunt racing Thoroughbreds: A preliminary study", Equine Veterinary Journal., vol. 41, No. 5, May 1, 2009 (May 1, 2009), pp. 493-497.

E. Barrey et al., "Utilisation of an accelerometric device in equine gait analysis", Equine Verterinary Journal., vol. 26, No. S17, Jun. 1, 1994 (Jun. 1, 1994), pp. 7-12.

Hailing Thomsen M et al., "Symmetry indices based on accelerometric data in trotting horses", Journal of Biomechanics, Pergamon Press, New York, NY, US, vol. 43, No. 13, Sep. 17, 2010 (Sep. 17, 2010), pp. 2608-2612.

* cited by examiner

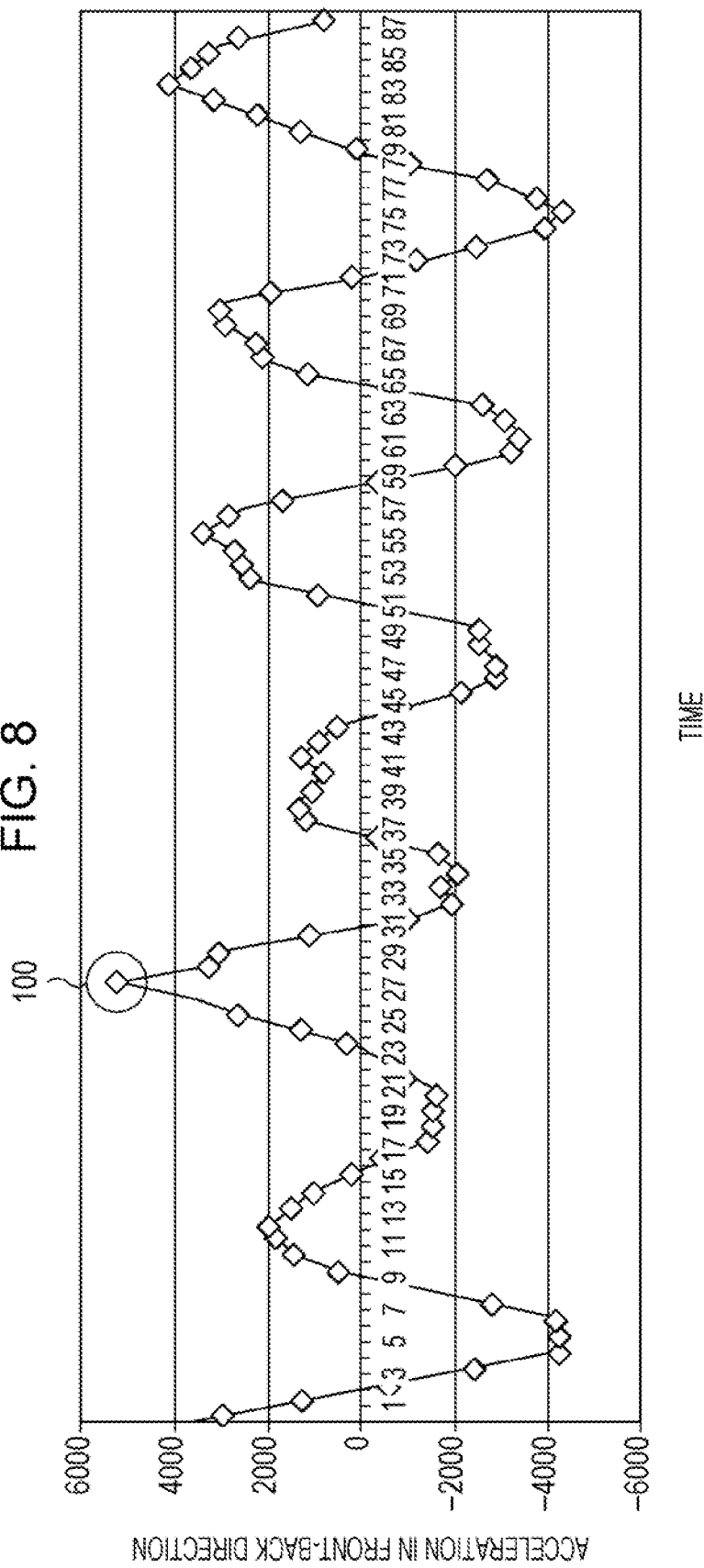

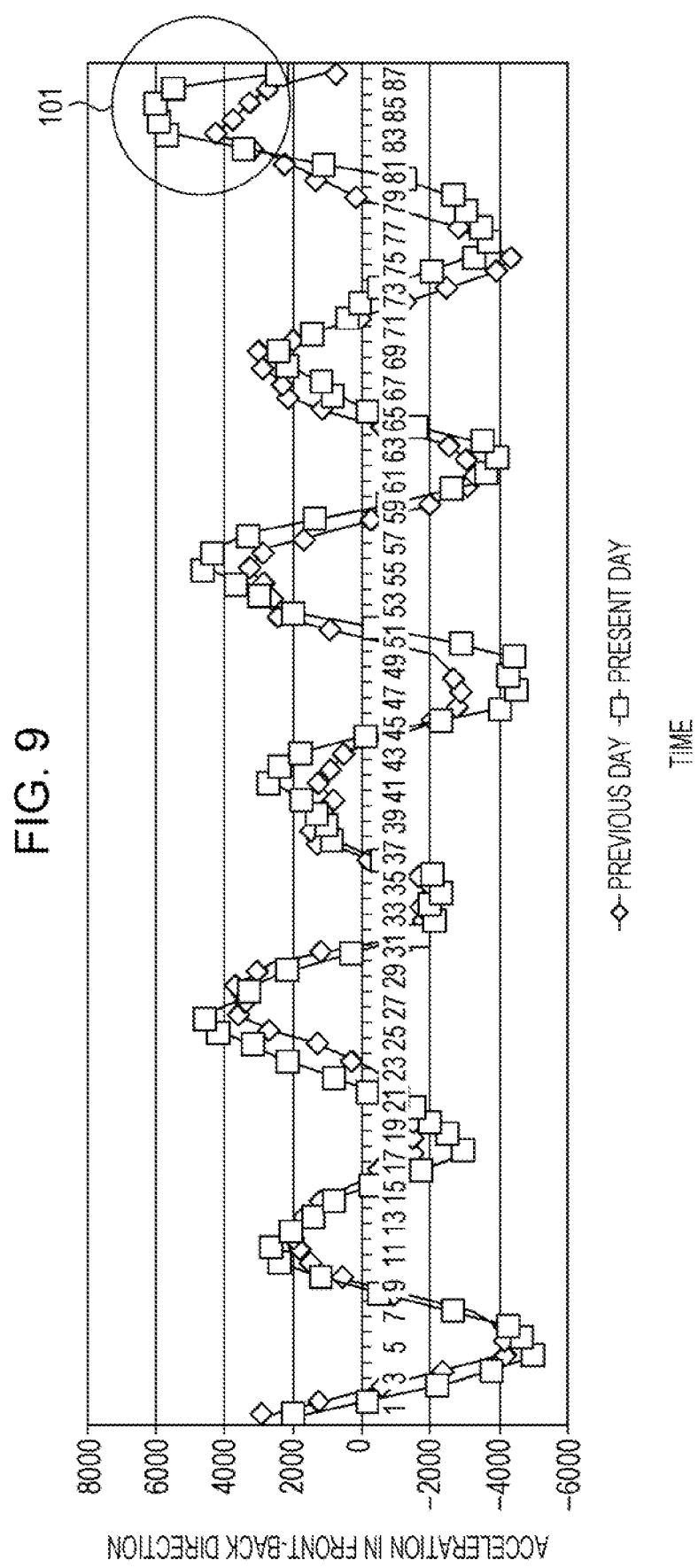

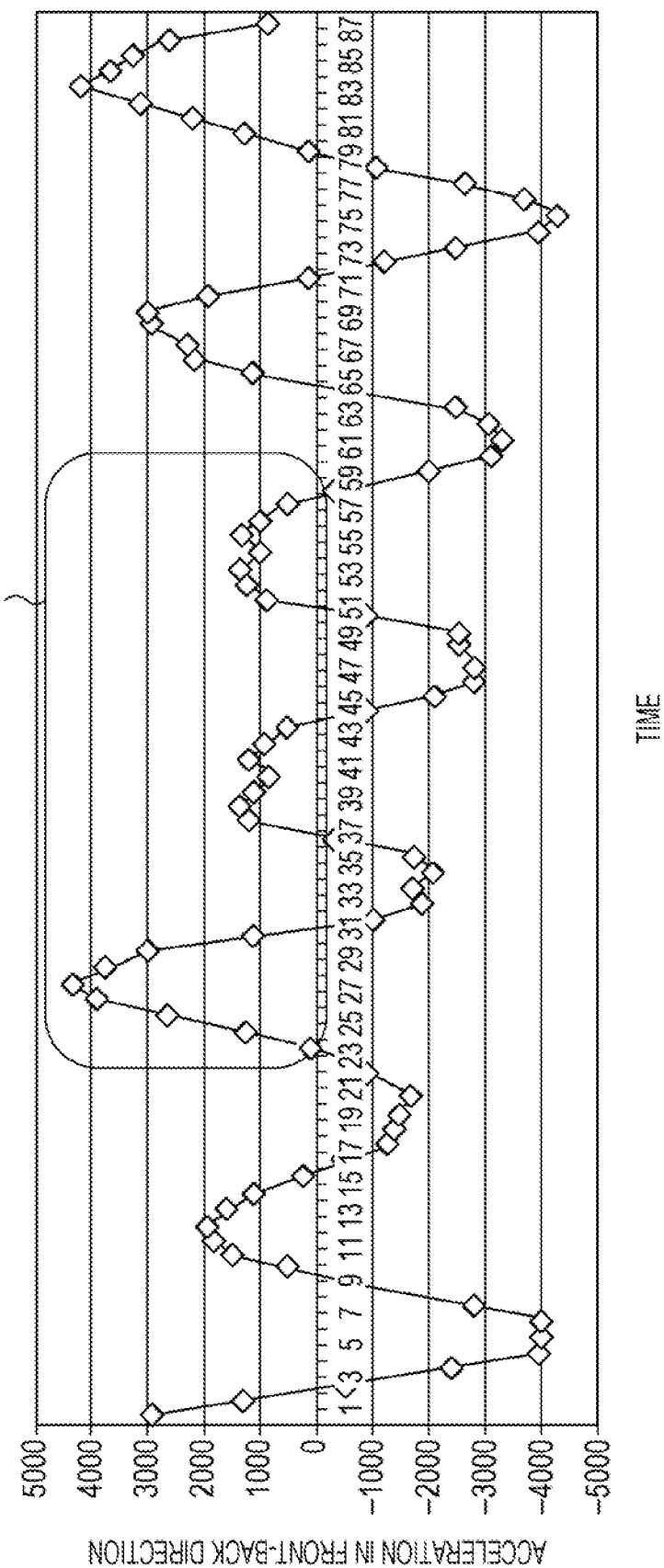

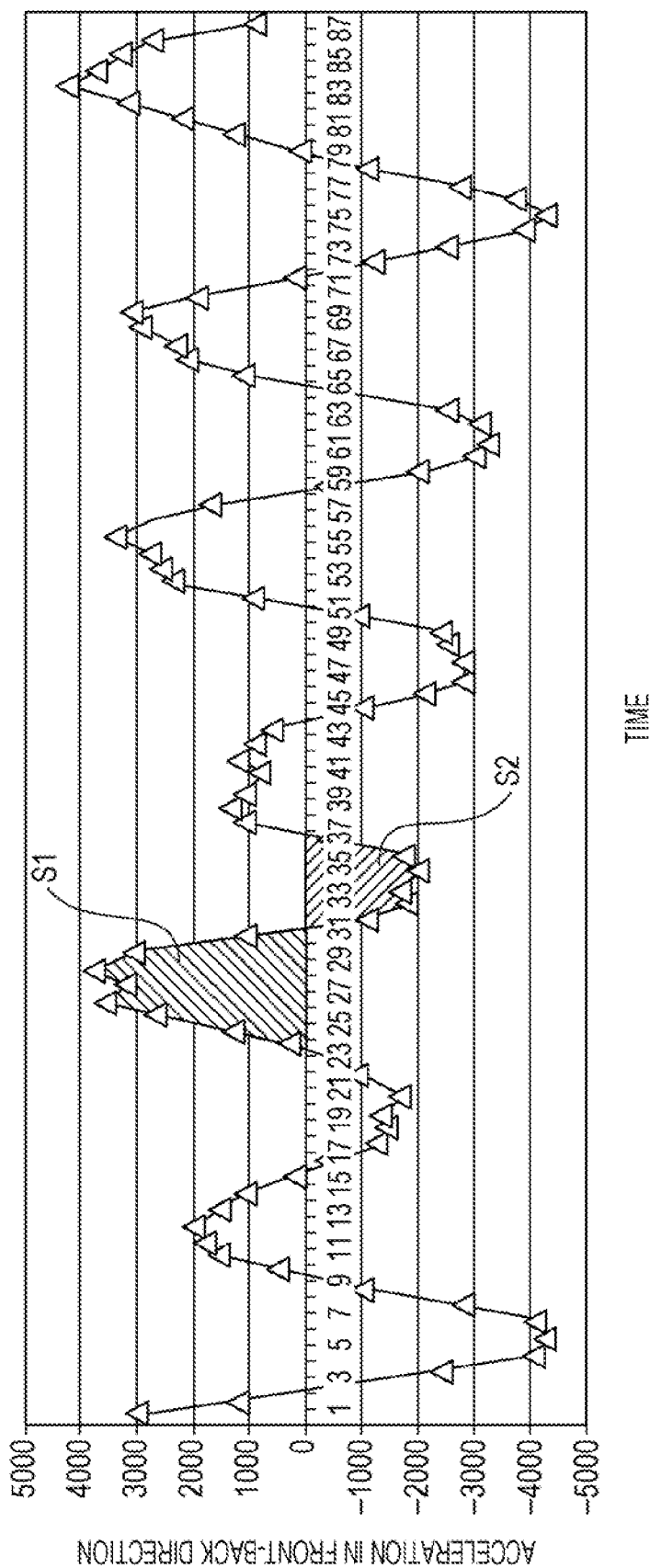

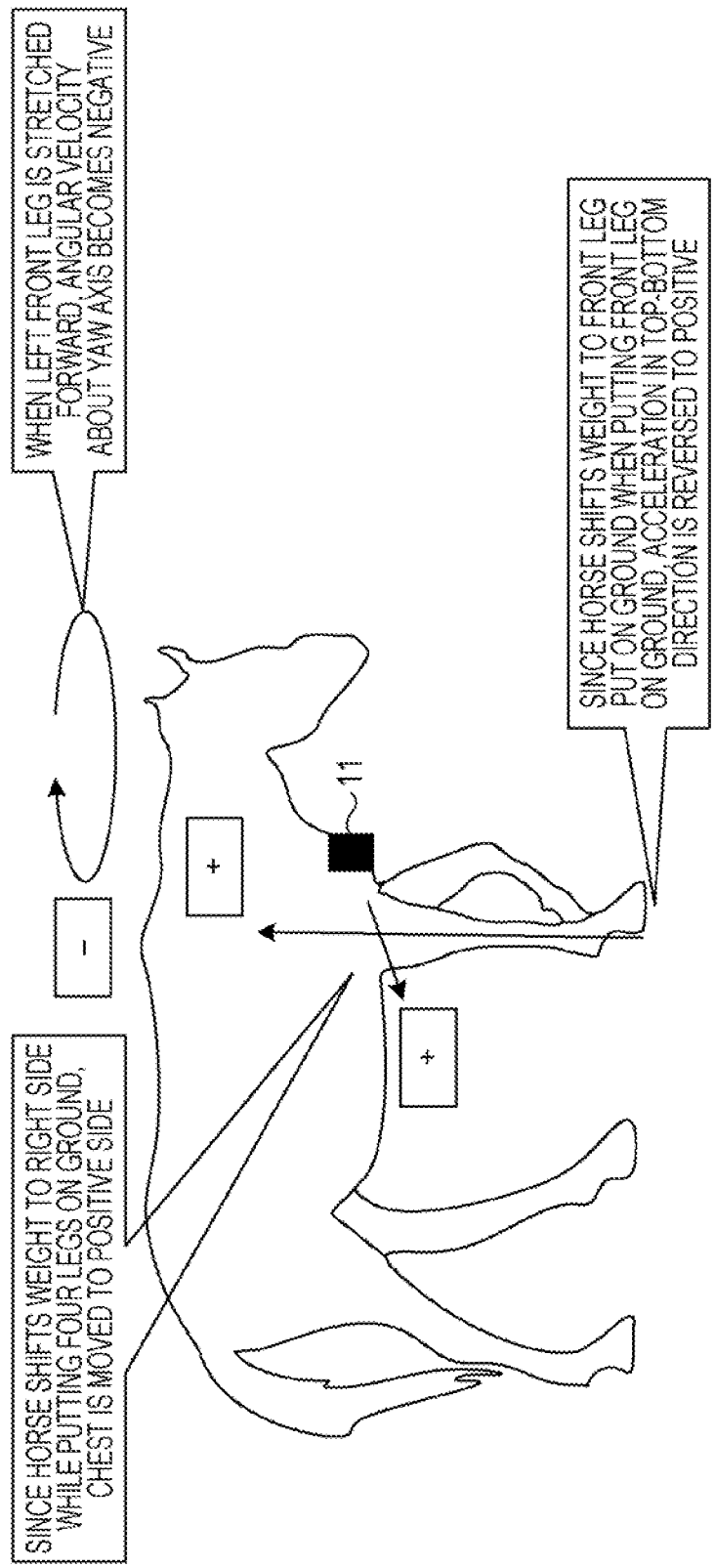

BODY CHARACTERISTIC MEASURING DEVICE, STORAGE MEDIUM STORING BODY CHARACTERISTIC MEASUREMENT PROGRAM, AND BODY CHARACTERISTIC MEASUREMENT METHOD

CROSS-REFERENCE TO RELATED APPLICATION

This application is based upon and claims the benefit of priority of the prior Japanese Patent Application No. 2016-150660, filed on Jul. 29, 2016, the entire contents of which are incorporated herein by reference.

FIELD

The embodiments discussed herein are related to a body characteristic measuring device, a storage medium storing a body characteristic measurement program, and a body characteristic measurement method.

BACKGROUND

There is the following problem with health management of horses typified by thoroughbreds. In general, such horses are trained by causing stress on minds and bodies of the horses in order to improve the performance of the horses. Especially, young horses during training periods are trained to run faster based on the growth of the horses.

As a horse's injury, there is a bowed tendon that is an inflammation in a front flexor tendon. When the expansion and contraction of muscles of a horse are beyond the ability of the horse, a bowed tendon may easily occur. A bowed tendon of a young horse during a growth period may result in a prolonged period of rest, during which the horse is not able to be trained, and may cause an unfortunate result for the horse and persons (owner of the horse, training staff, jokey, and other persons involved in the horse).

It is, therefore, desirable to determine whether or not a horse forcibly stretches a front leg and confirm whether or not an inflammation has occurred. If the inflammation has occurred, handling such as the suppression of training or a treatment is desirable for horse health management. Examples of related art are Japanese Laid-open Patent Publication Nos. 2016-96758, 2010-282456, and 2005-80635.

The forced stretch of the front legs may increase a bowed tendon risk. In order to avoid an injury, it is considered that the form of the horse during a movement of the horse is recorded and that a motion of a leg that may cause an injury is confirmed. Confirming the form is effective to determine characteristics that are the growth degree of the horse, the competitive ability of the horse, and the like and exclude injuries. A large recording device, however, is to be installed in order to record images of horses moving at high speeds and confirm the horses on a horse basis. In addition, an appropriate evaluation of body characteristics largely relies on experience and instinct and it is difficult to quantitatively evaluate the body characteristics.

Although the horses are exemplified in the above description, it is important to appropriately evaluate body characteristics in order to suppress injuries of quadrupeds, each of which moves with four legs.

According to an aspect, an object is to provide a body characteristic measuring device, a storage medium storing a body characteristic measurement program, and a body characteristic measurement method that enable an evaluation of body characteristics of quadrupeds.

SUMMARY

According to an aspect of the invention, a body characteristic measurement method causing a computer to execute a process, the process includes: determining a gait of a quadruped based on accelerations, acquired from a multi-axis acceleration sensor attached to the chest of the quadruped, in multiple axial directions; and determining, if the determined gait is gallop or canter, an injury risk of the quadruped based on a waveform of a positive half-wave region of acceleration in a movement direction of the quadruped in the case where an increase in the acceleration in the movement direction of the quadruped is defined as positive.

The object and advantages of the invention will be realized and attained by means of the elements and combinations particularly pointed out in the claims.

It is to be understood that both the foregoing general description and the following detailed description are exemplary and explanatory and are not restrictive of the invention, as claimed.

BRIEF DESCRIPTION OF DRAWINGS

FIG. 8 is a diagram illustrating an example of a waveform indicating changes in the acceleration in the front-back direction of the horse;

FIG. 9 is a diagram illustrating an example of waveforms indicating changes in the acceleration in the front-back direction of the horse;

FIG. 10 is a diagram illustrating an example of a waveform indicating changes in the acceleration in the front-back direction of the horse;

FIG. 11 is a diagram illustrating an example of changes in the acceleration in the front-back direction of the horse;

FIG. 14A is a diagram illustrating motions of the horse when the horse moves by walking;

DESCRIPTION OF EMBODIMENTS

Hereinafter, embodiments of a body characteristic measuring device disclosed herein, a body characteristic measurement program disclosed herein, and a body characteristic measurement method disclosed herein are described in detail with reference to the accompanying drawings. The techniques disclosed herein are not limited by the embodiments. Two or more of the following embodiments may be combined without causing contradiction.

First Embodiment

System Configuration

Figure 1:
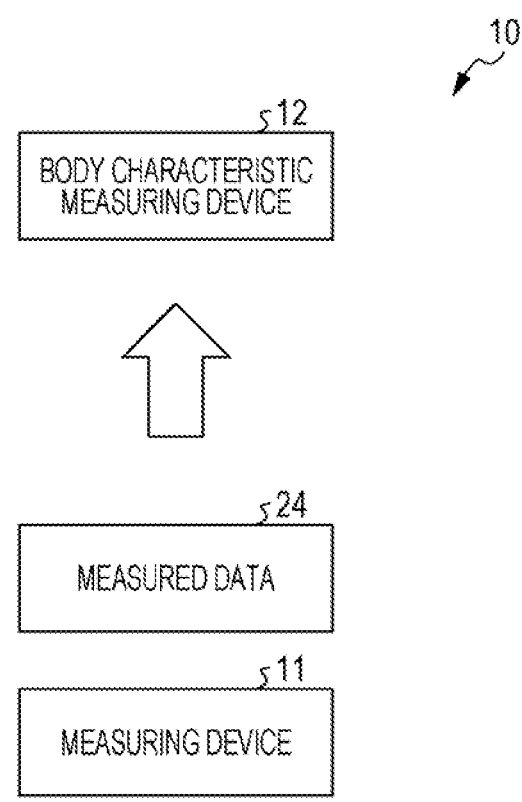
FIG. 1 is a diagram illustrating an example of a schematic configuration of a system.

First, an example of a system that executes health management according to a first embodiment is described. FIG. 1 is a diagram schematically illustrating the example of the system. A system 10 detects an abnormality of an animal that is a horse, a cow, or the like and moves with four legs. As the animal that moves with four legs, a horse is described as an example.

Horses are trained by causing stress on minds and bodies of the horses in order to improve the abilities of the horses. Especially, it is important to train race horses such as thoroughbreds while appropriately managing physical conditions of the race horses and suppressing injuries. Thus, it is requested to find abnormalities, such as bowed tendons, of race horses before the abnormalities become major. In the first embodiment, the system 10 measures body characteristics of the horse and detects an abnormality of the horse.

As illustrated in FIG. 1, the system 10 includes a measuring device 11 and a body characteristic measuring device 12. The measuring device 11 is attached to the horse. The measuring device 11 measures a behavior of the horse when the horse moves with four legs. For example, the measuring device 11 has a motion sensor therein. The motion sensor measures a behavior of the horse when the horse moves with four legs. The measuring device 11 stores data 24 measured by the motion sensor. The measuring device 11 and the body characteristic measuring device 12 transmit and receive data by wired communication or wireless communication or via a portable storage medium such as a flash memory. The data 24 measured by the measuring device 11 is transmitted to the body characteristic measuring device 12 by the wired communication or the wireless communication or via the portable storage medium.

The body characteristic measuring device 12 measures body characteristics of the horse based on the measured data 24. For example, the body characteristic measuring device 12 measures expanding and contracting motions of the horse during a movement of the horse and determines the flexibility of the horse. Then, the body characteristic measuring device 12 determines, based on the results of measuring the expanding and contracting motions of the horse during the movement, whether or not the expanding and contracting motions are beyond the ability of the horse. The body characteristic measuring device 12 provides a warning about the possibility of an inflammation such as a bowed tendon. For example, the body characteristic measuring device 12 is a computer such as a personal computer or a server computer. For example, the body characteristic measuring device 12 may be a mobile terminal device such as a tablet terminal, a smartphone, or a personal digital assistant (PDA). For example, the body characteristic measuring device 12 is arranged in a management source that is a stable, a ranch, or the like and in which the horse is managed. The body characteristic measuring device 12 may be implemented as a single computer or multiple computers. The first embodiment describes a case where the body characteristic measuring device 12 is a single computer as an example.

Figure 2:
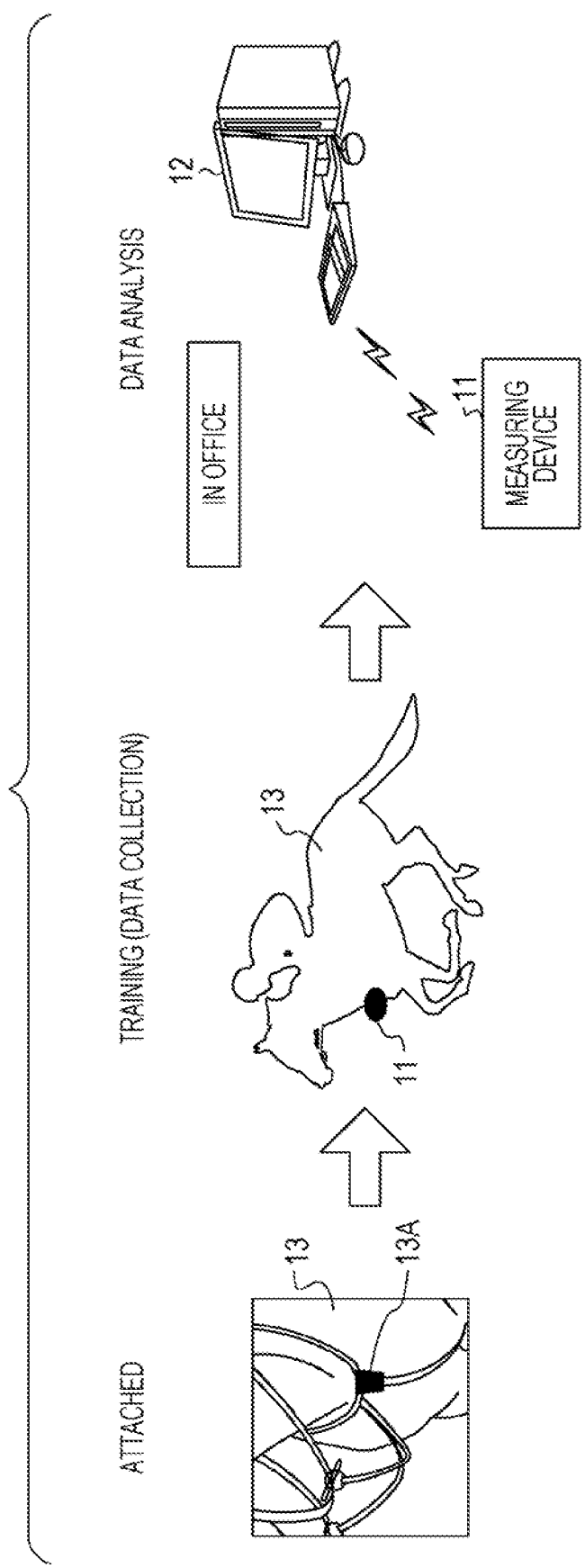
FIG. 2 is a diagram illustrating an example of the flow of horse health management by the system according to a first embodiment.

Next, an example of the flow of horse health management by the system 10 according to the first embodiment is described. FIG. 2 is a diagram illustrating the example of the flow of the horse health management by the system according to the first embodiment. The measuring device 11 is attached to the chest of a horse 13 targeted for the horse health management. For example, the measuring device 12 is stored in a harness 13A attached to the horse 13. In the example illustrated in FIG. 2, a martingale is used to enable the measuring device 11 to be attached to the chest of the horse 13. The horse 13 receives training of various types while the measuring device 11 is attached to the horse 13. The measuring device 11 collects data on behaviors by the motion sensor during the training and stores the measured data 24.

After the training, the measuring device 11 is carried to the stable or the like and the stored measured data 24 is uploaded to the body characteristic measuring device 12 by the wired or wireless communication or via the storage medium. The body characteristic measuring device 12 evaluates, based on the uploaded measured data 24, whether or not lameness has occurred. If the lameness has occurred, the body characteristic measuring device 12 estimates a leg with a problem causing the lameness.

Configuration of Measuring Device

Figure 3:
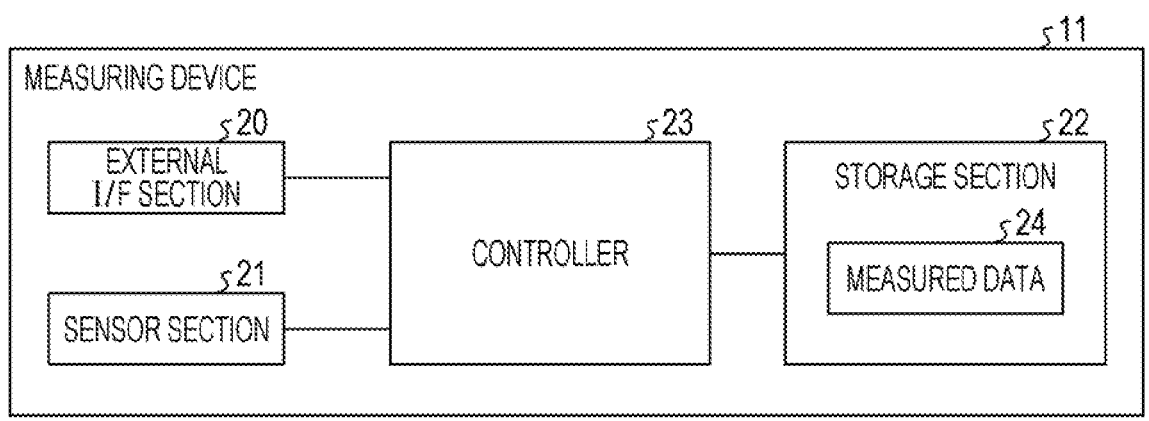
FIG. 3 is a diagram illustrating an example of a functional configuration of a measuring device according to the first embodiment.

Next, the configurations of the devices are described. First, the configuration of the measuring device 11 is described. FIG. 3 is a diagram illustrating an example of a functional configuration of the measuring device according to the first embodiment. As illustrated in FIG. 3, the measuring device 11 includes an external interface (I/F) section 20, a sensor section 21, a storage section 22, and a controller 23.

The external I/F section 20 is an interface that transmits and receives various types of information to and from the other device. The external I/F section 20 of the measuring device 11 according to the first embodiment is a port for receiving and outputting data from and to the storage medium such as a flash memory, a communication port for enabling wired communication via a cable or the like, or a communication interface for enabling wireless communication.

The sensor section 21 is the motion sensor that detects a behavior. For example, the sensor section 21 is a sensor that measures acceleration in multiple axes and angular velocities about the multiple axes. For example, the sensor section 21 is a 6-axial sensor that measures acceleration in three axial directions perpendicular to each other and angular velocities about the three axes. The sensor section 21 may be divided into a plurality of sensors. For example, the sensor section 21 may include a tri-axial accelerometer for measuring the acceleration in the three axial directions and a gyro sensor for measuring the angular velocities about the three axes. Alternatively, the sensor section 21 may be the tri-axial accelerometer for measuring the acceleration in the three axial directions.

The storage section 22 is a semiconductor memory that is a random access memory (RAM), a flash memory, or a nonvolatile static random access memory (NVSRAM) and in which data may be rewritten. The storage section 22 may be a storage device such as a hard disk, a solid state drive (SSD), or an optical disc. The storage section 22 stores various programs and an operating system (OS) to be executed by the controller 23. In addition, the storage section 22 stores various types of information. For example, the storage section 22 stores the measured data 24.

The measured data 24 is data storing various types of information on behaviors of the horse. For example, the measured data 24 stores the acceleration, measured by the sensor section 21, in the three axial directions and the angular velocities, measured by the sensor section 21, about the three axes, while the acceleration, measured by the sensor section 21, in the three axial directions and the angular velocities, measured by the sensor section 21, about the three axes are associated with measurement time when the acceleration and the angular velocities are measured in the measured data 24.

The controller 23 is a device that controls the whole measuring device 11. As the controller 23, an electronic circuit such as a central processing unit (CPU) or a micro processing unit (MPU) or an integrated circuit such as an application specific integrated circuit (ASIC) or a field programmable gate array (FPGA) may be used.

The controller 23 causes various types of data detected by the sensor section 21 to be stored in the measured data 24. For example, the controller 23 causes the sensor section 21 to measure the acceleration in the three axial directions and the angular velocities about the three axes at predetermined time intervals. Every time the sensor section 21 executes the measurement, the controller 23 associates values of the acceleration in the three axial directions and values of the angular velocities about the three axes with measurement time when the acceleration and the angular velocities are measured, and the controller 23 causes the values of the acceleration in the three axial directions, the values of the angular velocities about the three axes, and the measurement time to be stored in the measured data 24. The measurement time may be a time elapsed after the start of the measurement or may be a global time measured by a timestamp or the like. If the measurement time is the elapsed time, the measured data 24 in which the date and time when the measurement is started is included in a header is stored in the storage section 22. Hereinafter, it is assumed that the acceleration in the three axial directions and the angular velocities about the three axes are measured at time intervals of 0.05 seconds. The time intervals, however, are not limited to this.

Configuration of Body Characteristic Measuring Device

Figure 4:
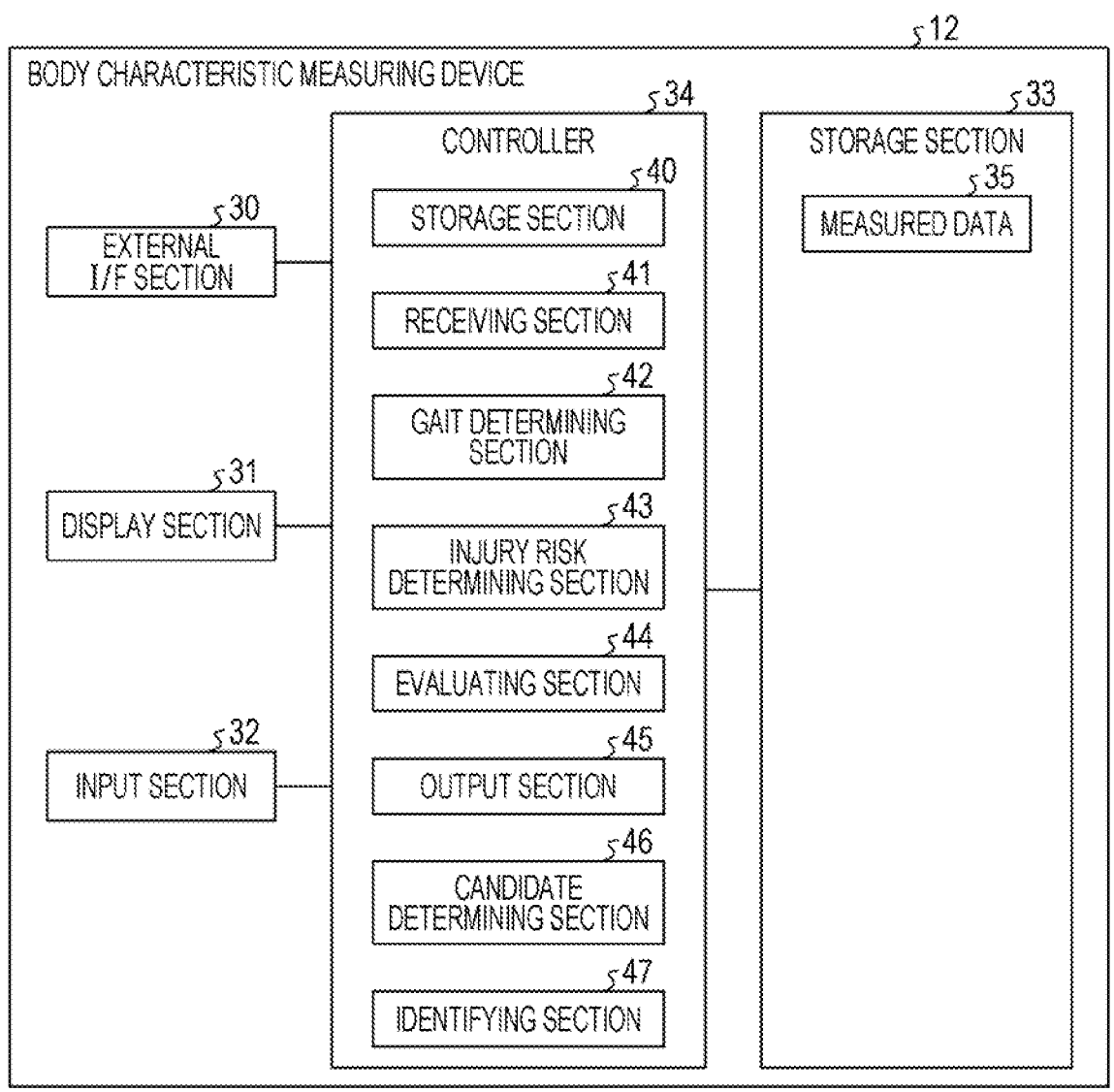
FIG. 4 is a diagram illustrating an example of a functional configuration of a body characteristic measuring device according to the first embodiment.

Next, the configuration of the body characteristic measuring device 12 is described. FIG. 4 is a diagram illustrating an example of a functional configuration of the body characteristic measuring device according to the first embodiment. As illustrated in FIG. 4, the body characteristic measuring device 12 includes an external I/F section 30, a display section 31, an input section 32, a storage section 33, and a controller 34.

The external I/F section 30 is an interface that transmits and receives various types of information to and from the other device, for example. The external I/F section 30 of the body characteristic measuring device 12 according to the first embodiment is a port for receiving and outputting data via a storage medium such as a flash memory, a communication port for enabling wired communication via a cable, or a communication interface for enabling wireless communication. For example, the external I/F section 30 receives the measured data 24 from the measuring device 11 via the storage medium or by the wired or wireless communication.

The display section 31 is a display device that displays various types of information. As the display section 31, a display device such as a liquid crystal display (LCD) or a cathode ray tube (CRT) may be used. The display section 31 displays various types of information. For example, the display section 31 displays various screens including an operational screen.

The input section 32 is an input device that inputs various types of information. As the input section 32, an input device that is a mouse, a keyboard, or the like and receives the input of an operation may be used. Alternatively, as the input section 32, various buttons included in the body characteristic measuring device 12 or a transparent touch sensor mounted on the display section 31 may be used. The input section 32 receives the input of various types of information. For example, the input section 32 receives the input of various operations that are an instruction to start a process and the like and are related to the evaluation. The input section 32 receives the input of an operation from a user and causes operational information indicating details of the received operation to be input to the controller 34. In the example illustrated in FIG. 4, the functional configuration is illustrated, and the display section 31 and the input section 32 are separated, but may be a unified device such as a touch panel.

The storage section 33 is a storage device for storing various types of data. For example, the storage section 33 is a storage device such as a hard disk, an SSD, or an optical disc. The storage section 33 may be a semiconductor device that is a RAM, a flash memory, an NVSRAM, or the like and in which data may be rewritten.

The storage section 33 stores various programs and an operating system (OS) to be executed by the controller 34. In addition, the storage section 33 stores various types of information. For example, the storage section 33 stores measured data 35.

The measured data 35 is data storing the measured data 24 acquired from the measuring device 11.

The controller 34 is a device that controls the body characteristic measuring device 12. As the controller 34, an electronic circuit such as a CPU or an MPU or an integrated circuit such as an ASIC or an FPGA may be used. The controller 34 includes an internal memory for storing control data and programs defining procedures for various processes and executes the various processes using the control data and the programs. The controller 34 functions as various processing sections by executing the various programs. For example, the controller 34 includes a storing section 40, a receiving section 41, a gait determining section 42, an injury risk determining section 43, an evaluating section 44, an output section 45, a candidate determining section 46, and an identifying section 47. In the first embodiment, the gait determining section 42 corresponds to a "first determining section", the injury risk determining section 43 corresponds to a "second determining section", the candidate determining section 46 corresponds to a "third determining section", the identifying section 47 corresponds to an "identifying section", and the evaluating section 44 corresponds to an "evaluating section".

The storing section 40 causes various types of data to be stored. For example, the storing section 40 causes the measured data 24 acquired from the measuring device 11 via the external I/F section 30 to be stored as the measured data 35 in the storage section 33.

The receiving section 41 receives various types of data. For example, the receiving section 41 receives various operational instructions. For example, the receiving section 41 causes the display section 31 to display various screens including the operational screen and receives an operational instruction such as an instruction to start processing the measured data 35.

The gait determining section 42 determines, based on the measured data 35, the gait of the horse when the horse moves. The determination of the gait is described below in detail.

Gaits when the horse moves are classified into "walk", "trot", "canter", and "gallop". The gaits when the horse moves are also referred to as horse gaits. The speed and vibration of the horse increase in the order of walk, trot, canter, and gallop. Thus, the acceleration in the three axial directions increases in the order of walk, trot, canter, and gallop. During trot, canter, and gallop, the horse's body floats during one stride and the acceleration in the three axial directions is temporarily zero or the horse is temporarily in zero gravity.

The acceleration in the three axial directions that is associated with measurement time stored in the measurement data 35 includes vibration components caused by motions of the four legs of the horse and gravity components caused by gravity. The vibration components correspond to one stride of the horse and periodically vary. The gravity components are fixed or nearly fixed. Thus, when values of the acceleration in the three axial directions pass through a cutoff frequency low pass filter (LPF) or high pass filter (HPF) that is appropriate for changes in the acceleration in the three axial directions, the acceleration in the three axial directions may be separated into the vibration components and the gravity components. The direction of the gravity components is a vertical direction.

The gait determining section 42 uses characteristics of the horse gaits to calculate acceleration in a top-bottom direction of the horse, acceleration in a left-right direction of the horse, and acceleration in a front-back direction (movement direction) of the horse from the acceleration, stored in the measured data 35, in the three axial directions and the angular velocities, stored in the measured data 35, about the three axes. First, the gait determining section 42 separates the acceleration, measured at measurement time, in the three axial directions into the vibration components caused by the movement of the horse and the gravity components. For example, the gait determining section 42 uses data obtained in a period of time when changes in the acceleration in the three axial directions are small, separates the gravity components from the acceleration, and separates, as the vibration components caused by the movement of the horse, differential components obtained by subtracting the gravity components from the acceleration, measured at the measurement time, in the three axial directions. The gait determining section 42 may cause values of the acceleration, measured at the measurement time, in the three axial directions to pass through the low pass filter and separate the gravity components from the acceleration.

The gait determining section 42 treats the vertical direction as the top-bottom direction of the horse and separates a vibration component in the top-bottom direction from the vibration components caused by the movement of the horse. In addition, when the movement speed of the horse is in a steady state, a motion of the horse in the left-right direction is large and a motion of the horse in the front-back direction is small. Thus, the gait determining section 42 calculates, as the left-right direction of the horse, the direction of a vibration component that is largest in the direction perpendicular to the vertical direction and is among vibration components excluding the vibration component in the top-bottom direction and included in the vibration components caused by the movement of the horse. In addition, the gait determining section 42 calculates, as the front-back direction, a direction perpendicular to the top-bottom direction of the horse and the left-right direction of the horse. The gait determining section 42 separates a vibration component in the left-right direction of the horse and a vibration component in the front-back direction of the horse from the vibration components caused by the movement of the horse. In this manner, the gait determining section 42 calculates acceleration in the front-back direction, acceleration in the left-right direction, and acceleration in the top-bottom direction from the acceleration, stored in the measured data 35, in the three axial directions and the angular velocities, stored in the measured data 35, about the three axes. In addition, the gait determining section 42 calculates an angular velocity about a yaw axis defined by using the top-bottom direction as an axis, from the acceleration, stored in the measured data 35, in the three axial directions and the angular velocities, stored in the measured data 35, about the three axes. Even if the position of the measuring device 11 relative to the horse body slightly changes or the orientation of the measuring device 11 attached to the horse slightly changes, the horse gait may be reliably determined. The gait determining section 42 may calculate acceleration in a pitching direction defined by using the left-right direction as an axis and acceleration in a rolling direction defined by using the front-back direction as an axis. The calculation of the top-bottom direction, left-right direction, and front-back direction of the horse is not limited to this. For example, the method described in "Japanese Laid-open Patent Publication No. 2015-84943" disclosed by the present applicant may be used to calculate the top-bottom direction, left-right direction, and front-back direction of the horse.

The gait determining section 42 calculates a value $\alpha$ of the acceleration in the top-bottom direction and the square $\beta$ of the absolute value of the acceleration and uses $\alpha$ and $\beta$ to determine whether the gait of the horse when the horse moves is walk, trot, canter, or gallop. Details of the determination of the gait are described in Japanese Laid-open Patent Publication No. 2015-84943" disclosed by the present applicant, and a detailed description of the determination of the gait is omitted. The gait determining section 42 may use another method to determine the gait. The gait determining section 42 identifies, as a movement direction (forward direction) of the horse, a direction in which large acceleration occurs in the front-back direction of the horse when the gait changes to a faster gait. The gait determining section 42 uses the movement direction as a standard to identify rightward and leftward directions of the horse with respect to the left-right direction of the horse. The gait determining section 42 may identify, from a waveform, the movement direction of the horse with respect to the front-back direction of the horse.

Figure 5:
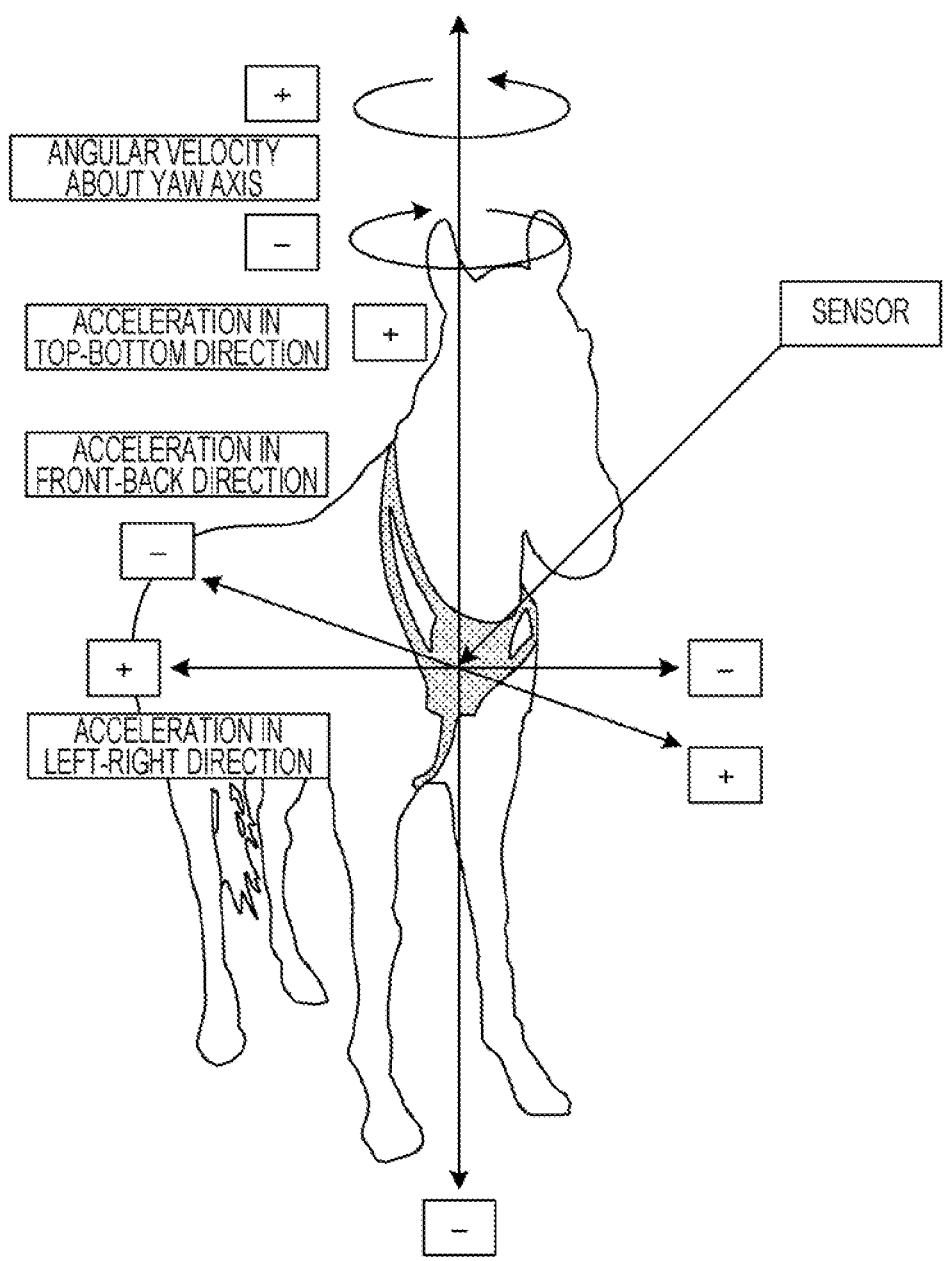
FIG. 5 is a diagram illustrating directions with respect to a horse.

FIG. 5 is a diagram illustrating the directions with respect to the horse. The measuring device 11 is attached to the chest of the horse. In the first embodiment, as illustrated in FIG. 5, an upward direction with respect to the horse is defined as positive in the top-bottom direction, and a downward direction with respect to the horse is defined as negative in the top-bottom direction. In the first embodiment, the movement direction (forward direction) of the horse is defined as positive in the front-back direction of the horse, and a direction (backward direction) opposite to the movement direction of the horse is defined as negative in the front-back direction of the horse. In the first embodiment, the rightward direction with respect to the movement direction of the horse is defined as positive in the left-right direction, and the leftward direction with respect to the movement direction of the horse is defined as negative in the left-right direction. In the first embodiment, a clockwise direction when viewed from the bottom of the horse toward the top of the horse in the top-bottom direction of the horse is defined as positive in the yaw axis direction, and a counterclockwise direction when viewed from the bottom of the horse toward the top of the horse in the top-bottom direction of the horse is defined as negative in the yaw axis direction.

The injury risk determining section 43 determines an injury risk of the horse based on the measured data 35. For example, if the gait determined by the gait determining section 42 is gallop or canter, the injury risk determining section 43 determines an injury risk of the horse based on a waveform of a positive half-wave region of acceleration in the movement direction in the case where an increase in the acceleration in the movement direction is positive.

Figure 6:
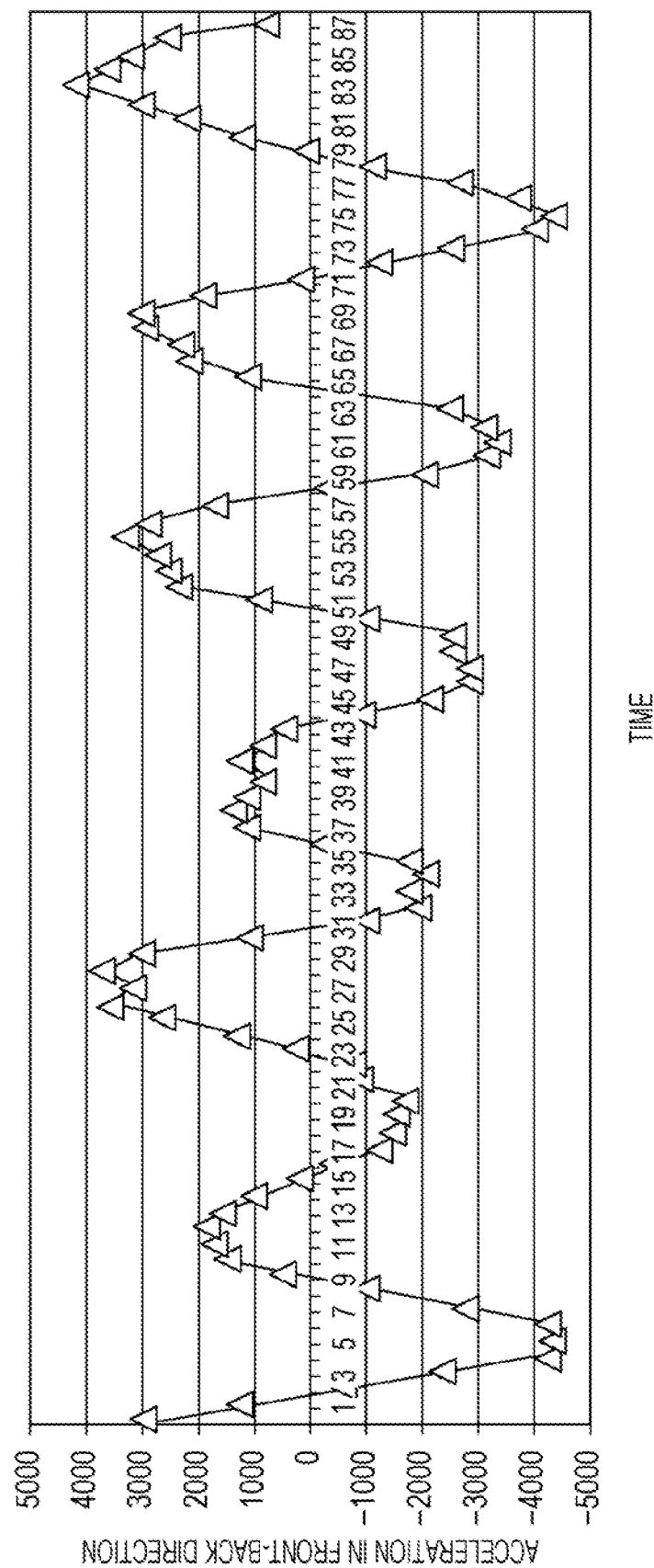
FIG. 6 is a diagram illustrating an example of a waveform indicating changes in acceleration in a front-back direction of the horse.

FIG. 6 is a diagram illustrating an example of a waveform indicating changes in the acceleration in the front-back direction of the horse. In the front-back direction of the horse, an increase in the acceleration in the movement direction is defined as positive.

The fastest quadruped is a feline. A characteristic of a gait of the feline is a flexible movement using a spring of its body. Similarly, horses run using springs of the horse bodies. For example, in Japan Racing Association, the running form of Deep Impact, which is a horse that won the Classics or a series of horse races, is evaluated as "flexible like a cat".

The horse is trained by causing stress on the horse. If the expansion and contraction of muscles of the horse are beyond the ability of the horse, an inflammation (bowed tendon) may easily occurs in a stretched front leg of the horse.

Figure 7A:
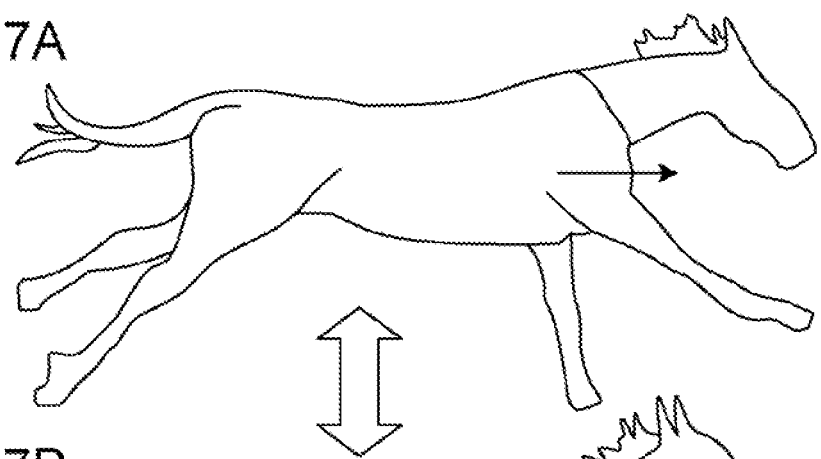
FIGS. 7A and 7B are diagrams illustrating motions of a moving horse.
Figure 7B:
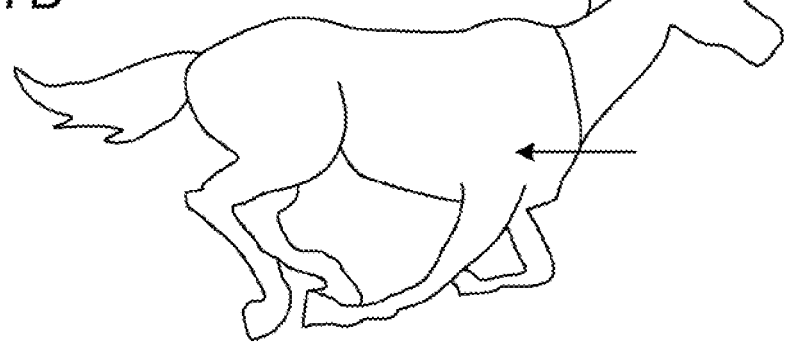

FIGS. 7A and 7B are diagrams illustrating motions of the moving horse. The measuring device 11 is attached to the chest of the horse. For example, the horse moves while repeating the motions illustrated in FIGS. 7A and 7B. For example, as illustrated in FIG. 7A, when the horse stretches a front leg together with the chest, the measuring device 11 is accelerated forward. In addition, as illustrated in FIG. 7B, when the horse pulls the back legs forward together with the chest, the measuring device 11 is accelerated backward.

The acceleration, measured by the measuring device 11, in the front-back direction of the horse coordinates with the expanding and contracting motions of the horse in the front-back direction of the horse. As the expanding and contracting motions of the horse become larger, the acceleration becomes larger. For example, motions of stretching the front legs of the horse coordinate with the acceleration in the movement direction of the horse. When the horse largely stretches the front legs forward, the acceleration in the movement direction of the horse becomes larger.

The injury risk determining section 43 determines an injury risk of the horse based on the waveform of the positive half-wave region of the acceleration in the movement direction of the horse.

For example, the injury risk determining section 43 determines an injury risk based on whether a burst exists in the waveform of the positive half-wave region of the acceleration in the movement direction of the horse. For example, if the peak of the positive half-wave region of the acceleration in the movement direction of the horse is equal to or larger than a predetermined threshold, the injury risk determining section 43 determines that the burst exists in the waveform. The threshold is set to a value appropriate to be treated as the burst. The threshold may be adjusted from an external. In addition, thresholds may be set for horses, the ages of the horses, the states of the horses, or the like. If the burst exists in the waveform, the injury risk determining section 43 determines that an injury risk exists.

FIG. 8 is a diagram illustrating an example of a waveform indicating changes in the acceleration in the front-back direction of the horse. A waveform illustrated in FIG. 8 indicates that the peak of a positive half-wave region exceeds the threshold (of, for example, 4000) at a time indicated by a reference numeral 100 and that a burst exists in the waveform. In this case, the injury risk determining section 43 determines that an injury risk exists.

In addition, for example, the injury risk determining section 43 compares the positive half-wave region with a model waveform and determines whether or not an injury risk exists. For example, the injury risk determining section 43 calculates a waveform of the acceleration in the movement direction of the horse from the measured data 24, compares a positive half-wave region of the waveform of the acceleration in the movement direction of the horse with a positive half-wave region of the model waveform, and determines whether or not the difference between the waveforms is equal to or larger than a predetermined value, thereby determining whether or not an injury risk exists. The model waveform may be a waveform indicating that there is a possibility that an injury risk may occur. Alternatively, the model waveform may be a waveform indicating that there is no possibility that an injury risk occurs.

For example, the injury risk determining section 43 compares a positive half-wave region calculated from the measured data 24 with a positive half-wave region calculated from previous measured data 24 (for example, measured data 24 of the previous day) of the same horse and calculates the difference between waveforms of the positive half-wave regions. For example, the injury risk determining section 43 calculates, as the difference between the waveforms, any of the difference between the areas of the positive half-wave regions, the difference between the amplitudes (peak values) of the waveforms, and the difference between wavelengths of the waveforms. If the difference between the waveforms is not in an acceptable range, the injury risk determining section 43 determines that an injury risk exists. The acceptable range is set to a range appropriate to treat the difference as a normal difference. The acceptable range may be adjusted by an external. In addition, acceptable ranges may be set for horses, the ages of the horses, the states of the horses, or the like.

FIG. 9 is a diagram illustrating an example of waveforms indicating changes in acceleration in the front-back direction of the horse. FIG. 9 illustrates waveforms indicating changes in the acceleration in the front-back direction of the horse on previous and present days. The difference between a waveform indicating changes in acceleration on the present day and a waveform indicating changes in acceleration on the previous day is not in the acceptable range at a time indicated by a reference numeral 101. In this case, the injury risk determining section 43 determines that an injury risk exists.

In addition, for example, a waveform pattern of the horse in which an inflammation has occurred in the past is stored. As an example, a waveform in which small waveforms are continuously generated after a large waveform is stored as the waveform pattern indicating that the inflammation has occurred. Then, the injury risk determining section 43 compares the positive half-wave region calculated from the measured data 24 with the waveform pattern of the horse in which the inflammation has occurred, and the injury risk determining section 43 determines a similarity. For example, the injury risk determining section 43 calculates the similarity between the positive half-wave region calculated from the measured data 24 and the waveform pattern of the horse in which the inflammation has occurred. If the similarity between the positive half-wave region and the waveform pattern is equal to or larger than a predetermined value, the injury risk determining section 43 determines that an injury risk exists.

FIG. 10 is a diagram illustrating an example of a waveform indicating changes in the acceleration in the front-back direction of the horse. In a waveform illustrated in FIG. 10, small waveforms are continuously generated after a large waveform within a time period indicated by a reference numeral 102. In this case, the injury risk determining section 43 determines that an injury risk exists.

If the injury risk determining section 43 determines that an injury risk exists, the injury risk determining section 43 may identify a leg having the injury risk. For example, if the injury risk determining section 43 determines that the injury risk exists, the injury risk determining section 43 determines the leg having the injury risk based on a rotational direction about the yaw axis when the injury risk is determined to exist from the waveform. For example, if the rotational direction about the yaw axis of the horse when the injury risk is determined to exist is the counterclockwise direction, the injury risk determining section 43 determines that the right front leg has an injury risk. If the rotational direction about the yaw axis of the horse when the injury risk is determined to exist is the clockwise direction, the injury risk determining section 43 determines that the left front leg has an injury risk.

The evaluating section 44 evaluates the flexibility of the horse. For example, the evaluating section 44 evaluates, for each of the gaits, the flexibility of the horse based on the difference between the positive half-wave component of the waveform of the acceleration in the movement direction and a negative half-wave component of the waveform of the acceleration in the movement direction. For example, the evaluating section 44 calculates the area of the positive half-wave region of the waveform of the acceleration in the movement direction and the area of the negative half-wave region of the waveform of the acceleration in the movement direction and sums the areas of the positive and negative half-wave components for each of the gaits. The positive half-wave component of the waveform of the acceleration in the movement direction corresponds to the area of the positive half-wave region, while the negative half-wave component of the waveform of the acceleration in the movement direction corresponds to a value obtained by multiplying the area of the negative half-wave region by −1. Thus, the difference between the positive and negative half-wave components of the waveform of the acceleration in the movement direction corresponds to a value obtained by adding the area of the positive half-wave region to the area of the negative half-wave region. For example, the evaluating section 44 calculates, as a flexibility evaluation value, the value obtained by adding the area of the positive half-wave region of the waveform of the acceleration in the movement direction to the area of the negative half-wave region of the waveform of the acceleration in the movement direction.

FIG. 11 is a diagram illustrating an example of changes in the acceleration in the front-back direction of the horse. FIG. 11 illustrates an example of the area S1 of the positive half-wave region and the area S2 of the negative half-wave region. The area S1 of the positive half-wave region indicates the magnitude of an expanding force of the horse during the movement of the horse. The area S2 of the negative half-wave region indicates the magnitude of a contracting force of the horse during the movement of the horse. Thus, the value obtained by adding the area S1 of the positive half-wave region to the area S2 of the negative half-wave region indicates the flexibility of the horse.

The output section 45 outputs various types of data. For example, if the injury risk determining section 43 determines that an injury risk exists, the output section 45 outputs, to the display section 31, information indicating that the horse has the injury risk. In addition, if the injury risk determining section 43 identifies a leg having the injury risk, the output section 45 outputs information indicating the leg having the injury risk. For example, the output section 45 outputs, to the display section 31, a screen displaying the name of the leg having the injury risk. In addition, the output section 45 outputs, to the display section 31, the results of evaluating the flexibility by the evaluating section 44 for the gaits. For example, the outputs section 45 outputs, to the display section 31, a screen displaying flexibility evaluation values for the gaits.

One of abnormal health conditions of the horse is an abnormal horse gait that is called lameness. The lameness occurs due to an abnormality such as an inflammation in a leg of the horse. When the lameness occurs, the horse drags the leg. Since the horse with the lameness protects the leg causing the lameness, the left-right balance of the horse tends to be unstable. Regarding a horse that has gotten an injury in a flexor tendon, a waveform of the horse when the horse moves to cool down tends to indicate lameness.

Thus, the body characteristic measuring device 12 may determine a cause of the lameness of the horse. If the lameness has occurred and the leg causing the lameness matches a leg determined to have an injury risk, the body characteristic measuring device 12 may output information indicating that the injury risk exists. For example, the body characteristic measuring device 12 determines whether or not lameness has occurred. If the leg causing the lameness matches the leg determined to have the injury risk, the body characteristic measuring device 12 may output information indicating that there is a possibility that a bowed tendon has occurred.

For example, the candidate determining section 46 evaluates the symmetry of the horse during a movement of the horse based on the measured data 35 and identifies a leg with a problem causing an inflammation. For example, the candidate determining section 46 identifies the leg with the problem from a movement waveform obtained during a movement of the horse. As a method of identifying the leg with the problem, the method described in "International Application No. PCT/JP2016/056146" or another method may be used, for example.

Figure 12:
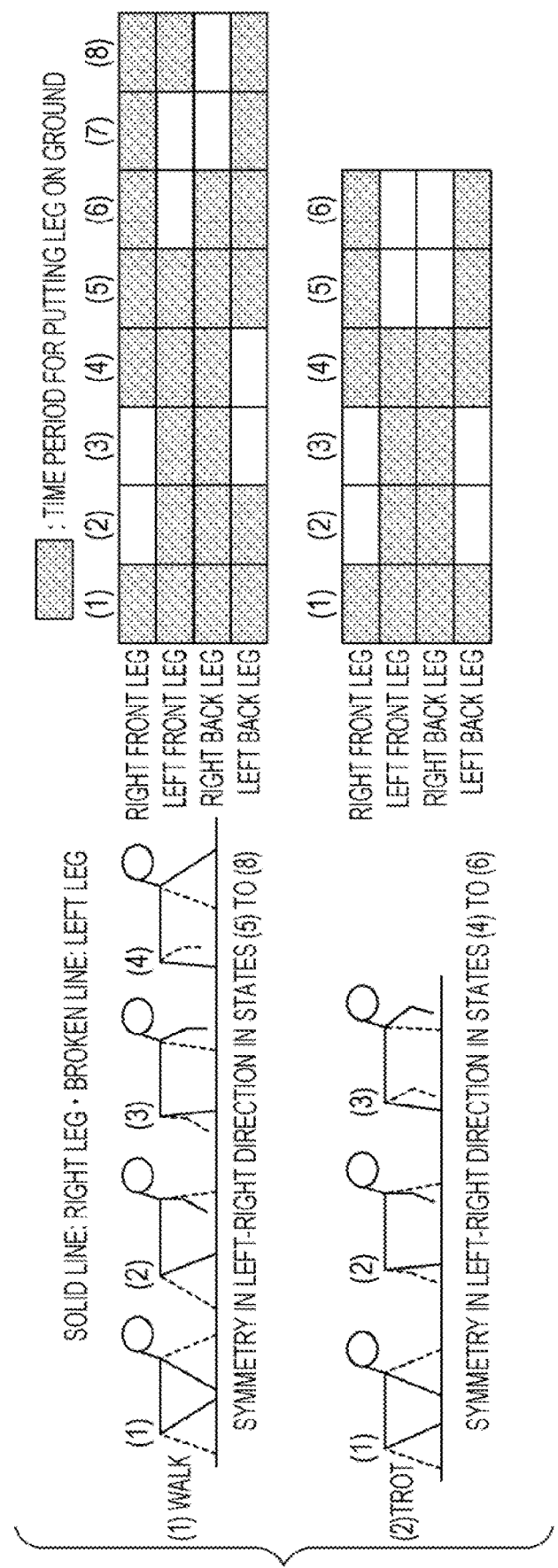
FIG. 12 is a diagram schematically illustrating positional relationships between four legs of the horse when the horse moves.

FIG. 12 is a diagram schematically illustrating positional relationships between the four legs of the horse during a movement of the horse. FIG. 12 illustrates (1) positional relationships between the four legs when the horse walks and (2) positional relationships between the four legs when the horse trots. FIG. 12 schematically illustrates the positional relationships between the four legs of the horse for the gaits on the left side of FIG. 12 and schematically illustrates whether or not each of the four legs (right front leg, left front leg, right back leg, and left back leg) is put on the ground within time periods (1) to (8) for the gaits. It looks that the four legs are put on the ground within the time periods (1) and (4) during trot in FIG. 12. However, when actual data is confirmed in detail, the legs are quickly switched in the time periods (1) and (4) and the body of the horse temporarily floats within the time periods (1) and (4).

As indicated by (2) in FIG. 12, during trot, the horse simultaneously moves a pair of the right front leg and the left back leg and simultaneously moves a pair of the left front leg and the right back leg.

Figure 13A:
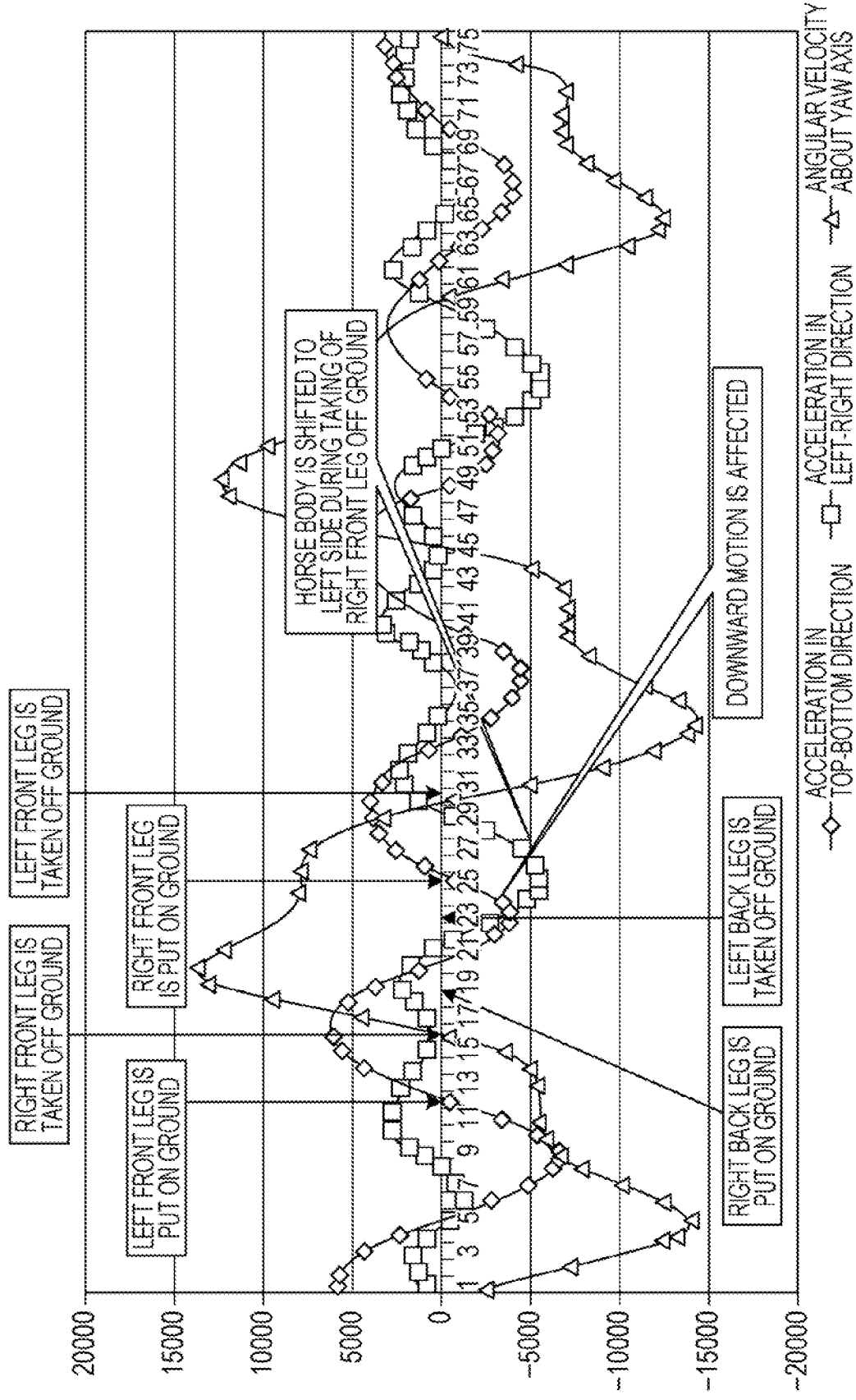
FIG. 13A is a diagram illustrating an example of movement waveforms when lameness occurs.

FIG. 13A is a diagram illustrating an example of movement waveforms of the horse when lameness occurs. FIG. 13A illustrates the timing of putting and taking the right front leg on and off the ground and the timing of putting and taking the left front leg on and off the ground. The calculation of the timing of putting and taking each leg of the horse on and off the ground during walk is described later. In the example illustrated in FIG. 13A, the acceleration in the left-right direction is asymmetric, a movement waveform of the right side (positive side in FIG. 13A) of the horse is larger than a movement waveform of the left side (negative side in FIG. 13A) of the horse, and the body of the horse is shifted to the left side during the time when the right front leg is taken off the ground. In this case, the horse may feel pain when the horse takes the right front leg off the ground or puts the right back leg on the ground.

When a large movement waveform of the left side of the horse is generated in the waveform of the acceleration in the left-right direction, the candidate determining section 46 primarily determines that the horse feels pain when the horse takes the right front leg off the ground or puts the right back leg on the ground. In addition, when a large movement waveform of the right side of the horse is generated in the waveform of the acceleration in the left-right direction, the candidate determining section 46 primarily determines that the horse feels pain when the horse takes the left front leg off the ground or puts the left back leg on the ground. In the example illustrated in FIG. 13A, the left front leg and the right back leg are primarily determined as candidates for a leg with a problem.

In the example illustrated in FIG. 13A, the candidate determining section 46 determines, based on a movement waveform of the acceleration in the top-bottom direction, that the amplitude of a downward motion (acceleration in the negative direction) of the horse body after the putting of the right back leg on the ground is smaller than the amplitude of an upward motion (acceleration in the positive direction) of the horse body immediately before the putting of the right back leg on the ground and the amplitude of a previous downward motion of the horse upon a previous stride, and that the length of a waveform of the downward motion is shorter than the length of a waveform of the upward motion and the length of a waveform of the previous downward motion. Thus, the candidate determining section 46 determines that the horse has felt pain upon the putting of the right back leg on the ground and has moved to avoid a load.

Figure 13B:
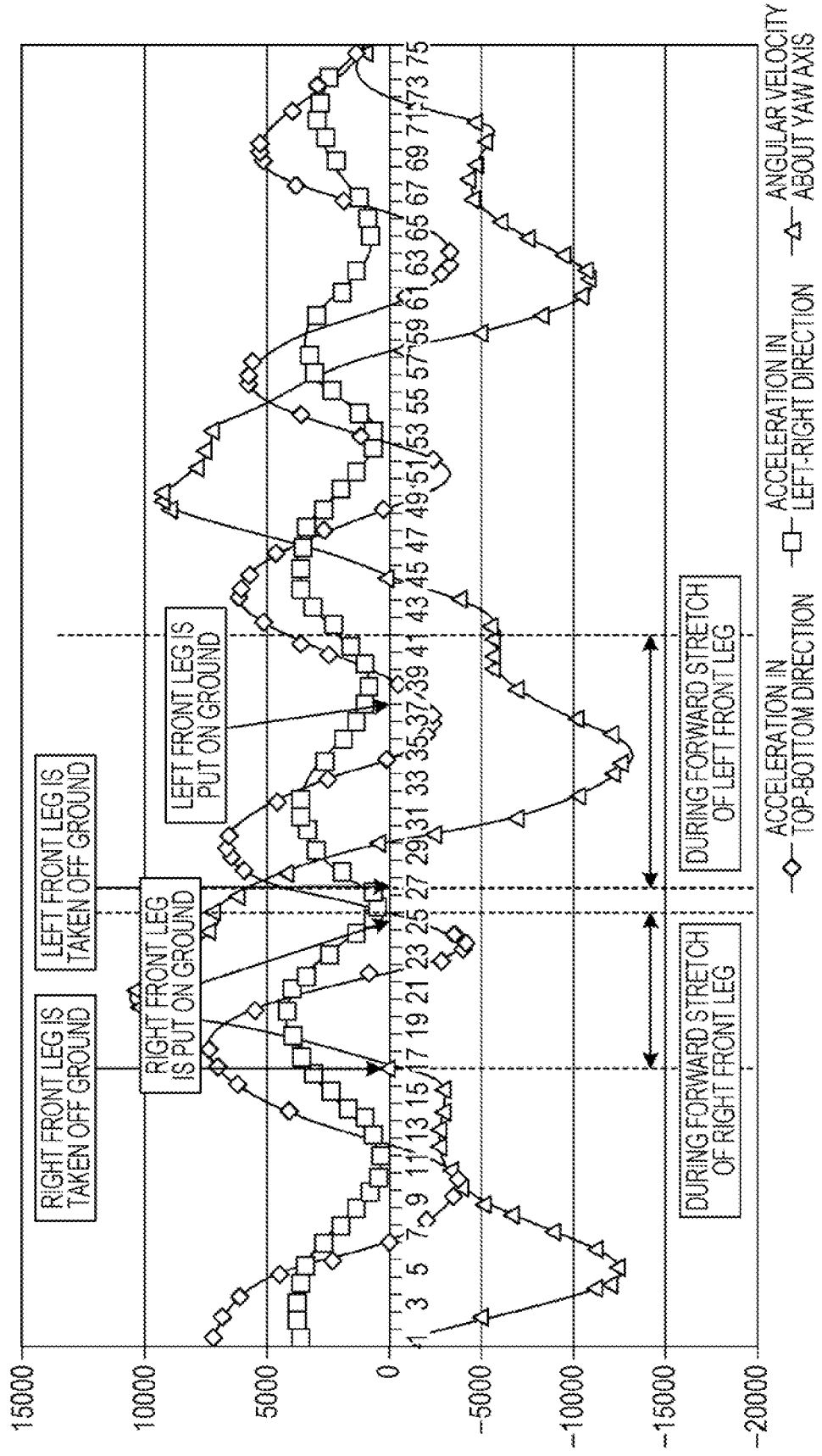
FIG. 13B is a diagram illustrating another example of the movement waveforms when the lameness occurs.

FIG. 13B is a diagram illustrating another example of the movement waveforms when the lameness occurs. FIG. 13B illustrates the timing of taking and putting the right front leg off and on the ground and the timing of taking and putting the left front leg off and on the ground. A time period from the time when a front leg is taken off the ground to the time when the front leg is put on the ground is hereinafter referred to as a forward stretching time period of the front leg. In the example illustrated in FIG. 13B, a forward stretching time period of the right front leg is different from a forward stretching time period of the left front leg. In addition, the peak of the angular velocity about the yaw axis during the forward stretching time period of the right front leg is smaller than the peak of the angular velocity about the yaw axis during the forward stretching time period of the left front leg. Thus, the example illustrated in FIG. 13B indicates a "state in which the right front leg is not easily stretched forward". It is considered that the "state in which the right front leg is not easily stretched forward" is a state in which the right front leg stretched forward has a problem or a state in which another leg to which a load is applied due to the forward stretch of the right front leg has a problem. However, the acceleration in the top-bottom direction and the acceleration in the left-right direction do not indicate asymmetry. Thus, in the example illustrated in FIG. 13B, the candidate determining section 46 determines that lameness caused by the right front leg has occurred (or that the horse feels pain when the horse puts the right front leg on the ground).

If the peak of the angular velocity about the yaw axis during the forward stretching time period of the right front leg is smaller than the peak of the angular velocity about the yaw axis during the forward stretching time period of the left front leg, the candidate determining section 46 determines a "state in which the right front leg is not easily stretched forward". Then, if the acceleration in the top-bottom direction and the acceleration in the left-right direction do not indicate asymmetry, the candidate determining section 46 identifies the right front leg as a leg with a problem. In addition, if the peak of the angular velocity about the yaw axis during the forward stretching time period of the left front leg is smaller than the peak of the angular velocity about the yaw axis during the forward stretching time period of the right front leg, the candidate determining section 46 determines a "state in which the left front leg is not easily stretched forward". Then, if the acceleration in the top-bottom direction and the acceleration in the left-right direction do not indicate asymmetry, the candidate determining section 46 identifies the left front leg as a leg with a problem.

In addition, a leg with a problem may be identified from a movement waveform obtained when the horse moves by walking. During walk, the horse separately moves the four legs, as indicated by (1) in FIG. 12.

FIG. 14A is a diagram illustrating motions of the horse when the horse moves by walking. As illustrated in FIG. 14A, in the case where the measuring device 11 is attached to the chest of the horse, the sign of the angular velocity about the yaw axis is reversed upon the stretch of a front leg of the horse. For example, when the horse stretches the left front leg forward, the sign of the angular velocity about the yaw axis is reversed to negative. In addition, when the horse puts a front leg on the ground, the horse places the weight of the horse on the front leg put on the ground and moves the horse body upward and the acceleration in the top-bottom direction is reversed to positive. In addition, when the horse stretches the left front leg forward, the measuring device 11 attached to the chest of the horse is accelerated toward the positive side in the left-right direction.

Figure 14B:
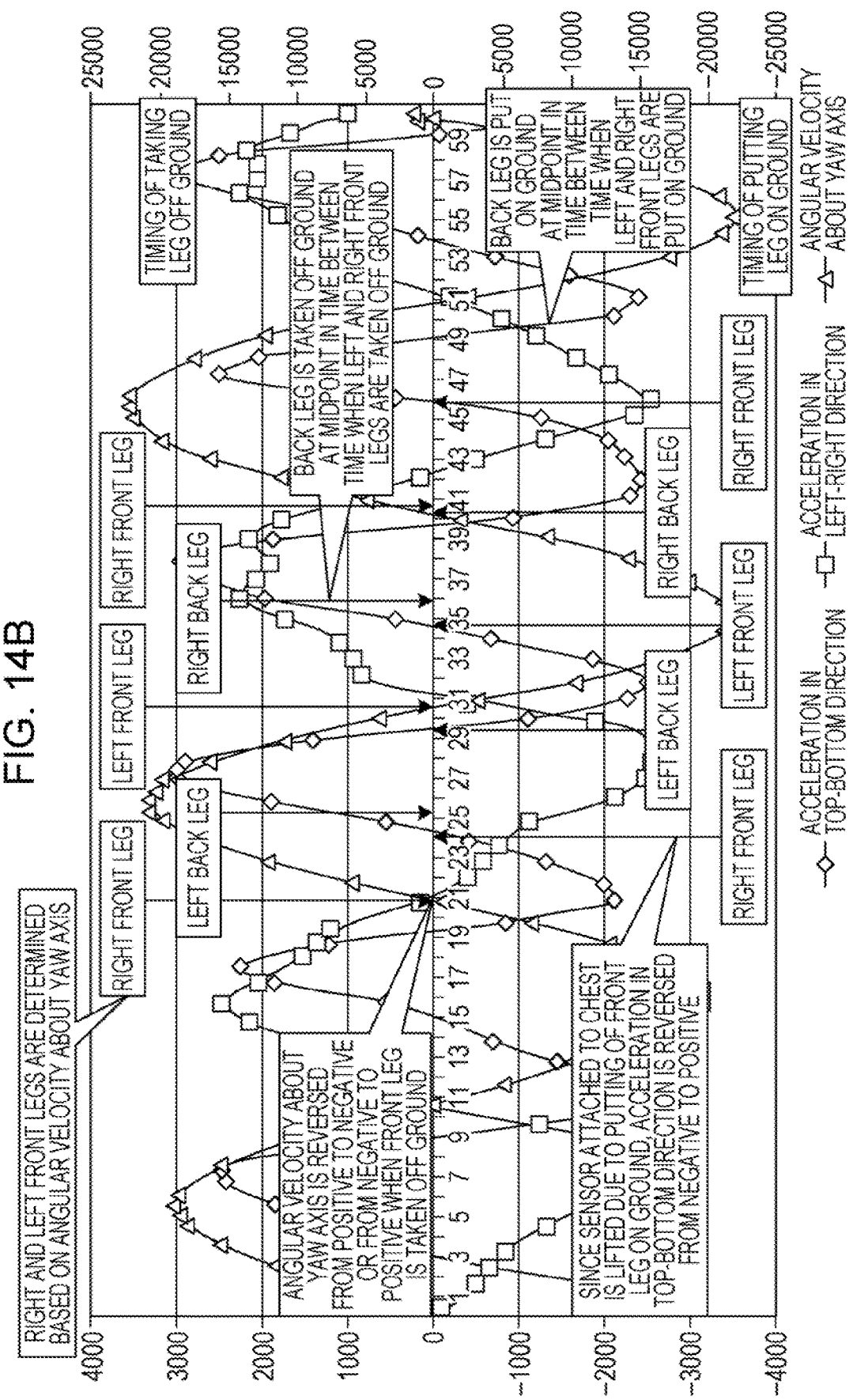
FIG. 14B is a diagram illustrating an example of a movement waveform indicating changes in acceleration in a top-bottom direction, a movement waveform indicating changes in acceleration in a left-right direction, and a movement waveform indicating changes in an angular velocity about a yaw axis when the horse moves by walking.

FIG. 14B is a diagram illustrating an example of a movement waveform indicating changes in the acceleration in the top-bottom direction, a movement waveform indicating changes in the acceleration in the left-right direction, and a movement waveform indicating changes in the angular velocity about the yaw axis when the horse moves by walking. When the horse stretches a front leg forward, the sign of the angular velocity about the yaw axis is reversed. If the angular velocity about the yaw axis increases in the counterclockwise direction, the horse stretches the right front leg forward. If the angular velocity about the yaw axis increases in the clockwise direction, the horse stretches the left front leg forward. When the horse puts a front leg on the ground, the horse places the weight of the horse on the front leg put on the ground and moves the horse body upward, and the acceleration in the top-bottom direction is reversed from negative to positive and results in a positive waveform. In addition, when the horse puts the right front leg on the ground, the angular velocity about in the yaw axis increases in the counterclockwise direction. When the horse puts the left front leg on the ground, the angular velocity about the yaw axis increases in the clockwise direction. In addition, at midpoints in time between the time when the horse takes the left front leg off the ground and the time when the horse takes the right front leg off the ground, the horse takes the left and right back legs off the ground. In addition, at midpoints in time between the time when the horse puts the left front leg on the ground and the time when the horse puts the right front leg on the ground, the horse puts the left and right back legs on the ground.

The candidate determining section 46 determines, based on movement waveforms obtained when the horse moves by walking, time when the horse takes and puts the four legs off and on the ground. For example, the candidate determining section 46 determines the time when the horse takes and puts the four legs off and on the ground, based on a movement waveform of the acceleration in the top-bottom direction when the horse moves by walking and a movement waveform of the angular velocity about the yaw axis when the horse moves by walking. For example, if the angular velocity about the yaw axis increases in the counterclockwise direction after the angular velocity about the yaw axis is reversed from positive to negative or from negative to positive, the candidate determining section 46 determines that the time when the angular velocity about the yaw axis is reversed from positive to negative or from negative to positive is the time when the horse takes the right front leg off the ground. If the angular velocity about the yaw axis increases in the clockwise direction after the angular velocity about the yaw axis is reversed from positive to negative or from negative to positive, the candidate determining section 46 determines that the time when the angular velocity about the yaw axis is reversed from positive to negative or from negative to positive is the time when the horse takes the left front leg off the ground. For example, if the rotational direction about the yaw axis is the counterclockwise direction when the acceleration in the top-bottom direction is reversed from negative to positive, the candidate determining section 46 determines that the time when the acceleration in the top-bottom direction is reversed from negative to positive is the time when the horse puts the right front leg on the ground. If the rotational direction about the yaw axis is the clockwise direction when the acceleration in the top-bottom direction is reversed from negative to positive, the candidate determining section 46 determines that the time when the acceleration in the top-bottom direction is reversed from negative to positive is the time when the horse puts the left front leg on the ground. For example, the candidate determining section 46 determines that the midpoint in time between the time when the horse takes the right front leg off the ground and the time when the horse takes the left front leg off the ground is the time when the horse takes the left back leg off the ground. The candidate determining section 46 determines that the midpoint in time between the time when the horse takes the left front leg off the ground and the time when the horse takes the right front leg off the ground is the time when the horse takes the right back leg off the ground. The candidate determining section 46 determines that the midpoint in time between the time when the horse puts the right front leg on the ground and the time when the horse puts the left front leg on the ground is the time when the horse puts the left back leg on the ground. The candidate determining section 46 determines that the midpoint in time between the time when the horse puts the left front leg on the ground and the time when the horse puts the right front leg on the ground is the time when the horse puts the right back leg on the ground. FIG. 14B illustrates, on the upper side, the timing of taking the legs (right front leg, left front leg, right back leg, and left back leg) off the ground and illustrates, on the lower side, the timing of putting the legs on the ground.

The candidate determining section 46 identifies, based on the determined time when the horse takes and puts the four legs off and on the ground, a leg that coordinates with a distortion of a movement waveform. For example, the candidate determining section 46 identifies an abnormal leg with a problem based on movement waveforms in the left-right direction and the front-back direction.

Figure 14C:
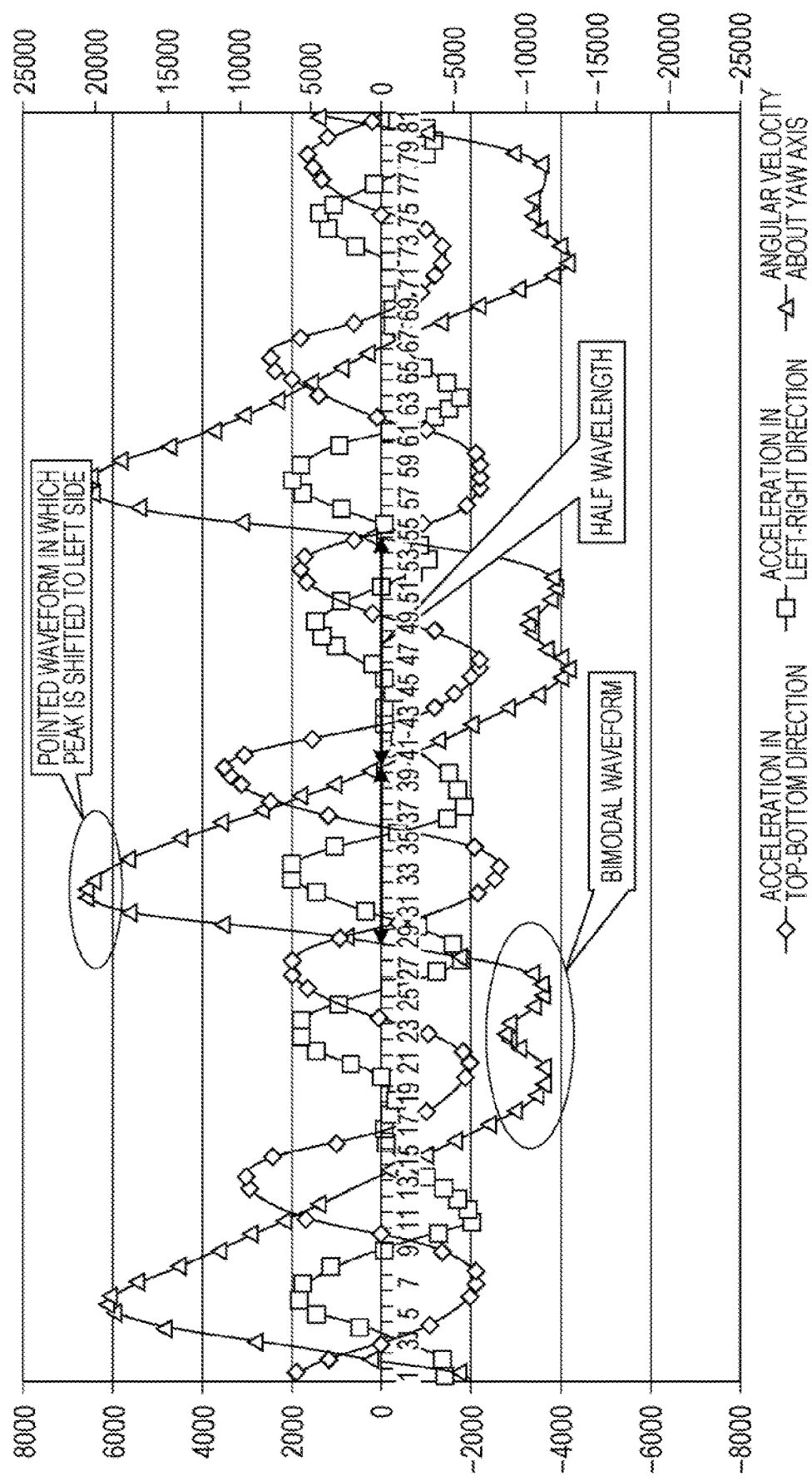
FIG. 14C is a diagram illustrating an example of movement waveforms when lameness occurs.

FIG. 14C is a diagram illustrating an example of movement waveforms when lameness occurs. In the example illustrated in FIG. 14C, when the angular velocity about the yaw axis is negative or the left front leg is lifted, the rotational rate is reduced and a bimodal waveform is generated. At the midpoint in time between the time when the left front leg is lifted and the time when the right front leg is lifted, or when the right back leg is moved, the bimodal waveform is generated.

In the example illustrated in FIG. 14C, the peak of a pointed waveform in which the angular velocity about the yaw axis is positive is shifted to the left side. This indicates that since the body is supported by the painful right back leg on the right side, the horse wants to quickly put the right front leg on the ground and avoid the pain of the right back leg. In addition, when a half wavelength of a single-cycle movement waveform is paid attention, a time period in which the value of the waveform is positive is shorter than a time period in which the value of the waveform is negative. This indicates that the horse moves the painful right back leg slowly and wants to avoid the pain of the right back leg.

If the bimodal waveform is generated, the candidate determining section 46 identifies, as a leg with a problem, a leg corresponding to the time when the bimodal waveform is generated. In the example illustrated in FIG. 14C, since the bimodal waveform is generated at the midpoint in time between the time when the left front leg is lifted and the time when the right front leg is lifted or the bimodal waveform is generated upon the movement of the right back leg, the candidate determining section 46 identifies the right back leg as a leg with a problem.

If a pointed waveform in which the peak is shifted to the left side is generated, the candidate determining section 46 identifies, as a leg with a problem, a leg corresponding to the time when the pointed waveform is generated. In addition, if the difference between a time period in which the value of a single-cycle waveform is positive and a time period in which the value of the single-cycle waveform is negative is equal to or higher than a predetermined percentage (of, for example, 85%), the candidate determining section 46 identifies, as a leg with a problem, a leg corresponding to the time periods for the waveform.

The identifying section 47 identifies a leg with a problem based on the result of determining the leg with the problem by the injury risk determining section 43 and the result of identifying the leg with the problem by the candidate determining section 46 and determines whether or not a bowed tendon risk exists. For example, if a leg identified by the candidate determining section 46 as a leg with a problem matches a leg determined by the injury risk determining section 43 to have an injury risk, the identifying section 47 identifies that a bowed tendon has occurred in the matched leg.

The output section 45 outputs information indicating the leg identified as the leg with the problem. For example, the output section 45 outputs, to the display section 31, a screen displaying the name of the leg identified as the leg with the problem. The output section 45 may output information indicating that there is a possibility that a bowed tendon has occurred in the leg identified as the leg with the problem.

Figure 15:
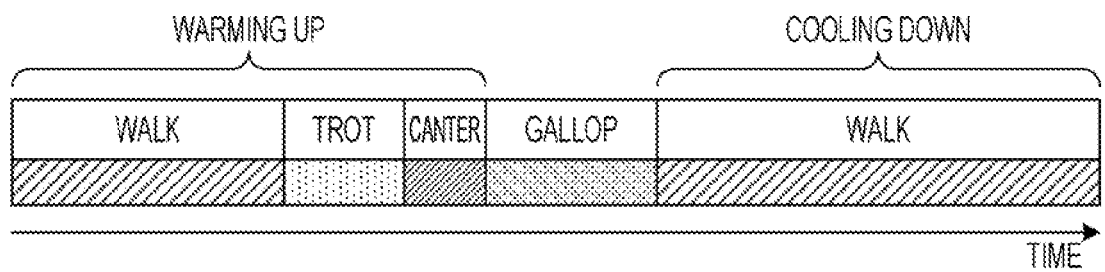
FIG. 15 is a diagram schematically illustrating an example of changes in the gait of the horse during training.

FIG. 15 is a diagram schematically illustrating an example of changes in the gait of the horse during training. For example, in the training, a person makes the horse walk, trot, and canter in order to make the horse warm up. Then, in the training, the person makes the horse gallop in order to cause high stress on the horse. After that, in the training, the person makes the horse walk and cool down.

For example, the body characteristic measuring device 12 determines, based on the measured data 24 and a waveform of the acceleration in the front-back direction of the horse during gallop, whether or not an injury risk exists. If the injury risk exists, the body characteristic measuring device 12 determines a leg having the injury risk. In addition, the body characteristic measuring device 12 determines, based on the measured data 24, whether or not lameness has occurred during walk for cooling down. If the lameness has occurred, the body characteristic measuring device 12 identifies a leg causing the lameness as a leg with a problem. If the leg identified as the leg with the problem matches the leg determined to have the injury risk, the body characteristic measuring device 12 identifies the matched leg as the leg with the problem.

When the expansion and contraction of muscles of the horse are beyond the ability of the horse, a bowed tendon may easily occur. A bowed tendon of a young horse during a growth period may result in a prolonged period of rest, during which the horse is not able to be trained, and may cause an unfortunate result for the horse and persons. It is, therefore, desirable to determine whether or not the horse forcibly stretches a front leg and confirm whether or not an inflammation has occurred. If the inflammation has occurred, handling such as the suppression of training or a treatment is desirable for the horse health management. Traditionally, a person who manages a horse has actually touched a leg of the horse and has confirmed whether or not an inflammation has occurred in the horse leg.

To evaluate body characteristics of the horse, it is considered that a high-definition camera is installed at a running course in a training center and that the form of the horse during a movement of the horse is analyzed by image analysis, for example. If the form of a specific horse during a movement of the horse is analyzed on a specific course, it is effective to use the aforementioned method. In general, however, there are multiple running courses, multiple horses are trained, and it is not practical to analyze forms of all the horses by image analysis on each day and convert the flexibility of the horses into values. The flexibility of the horses during movements of the horses is major key information of the physical performance of the horses. Traditionally, however, the measurement of the physical performance of the horses has depended on horse riders' perception.

On the other hand, according to the system 10 according to the first embodiment, the measuring device 11 is attached to the horse, the horse is trained, and an injury risk may be determined without a person's perception. In addition, according to the system 10 according to the first embodiment, the flexibility of the horse may be measured and converted into a value, and the physical performance of the horse may be objectively evaluated without a person's perception.

Process Flow

Figure 16A:
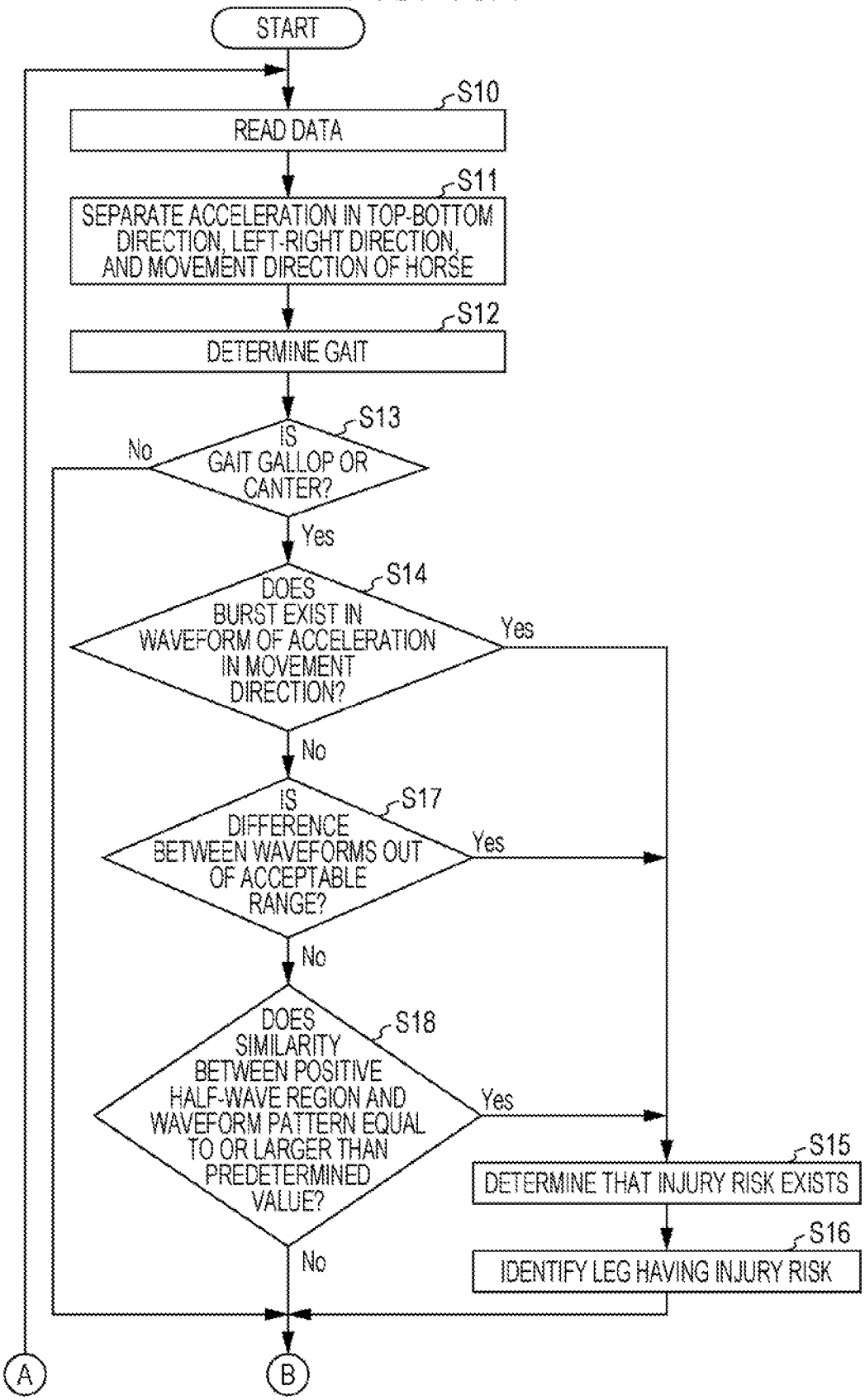
FIGS. 16A and 16B are a flowchart of an example of a procedure for a body characteristic measurement process.
Figure 16B:
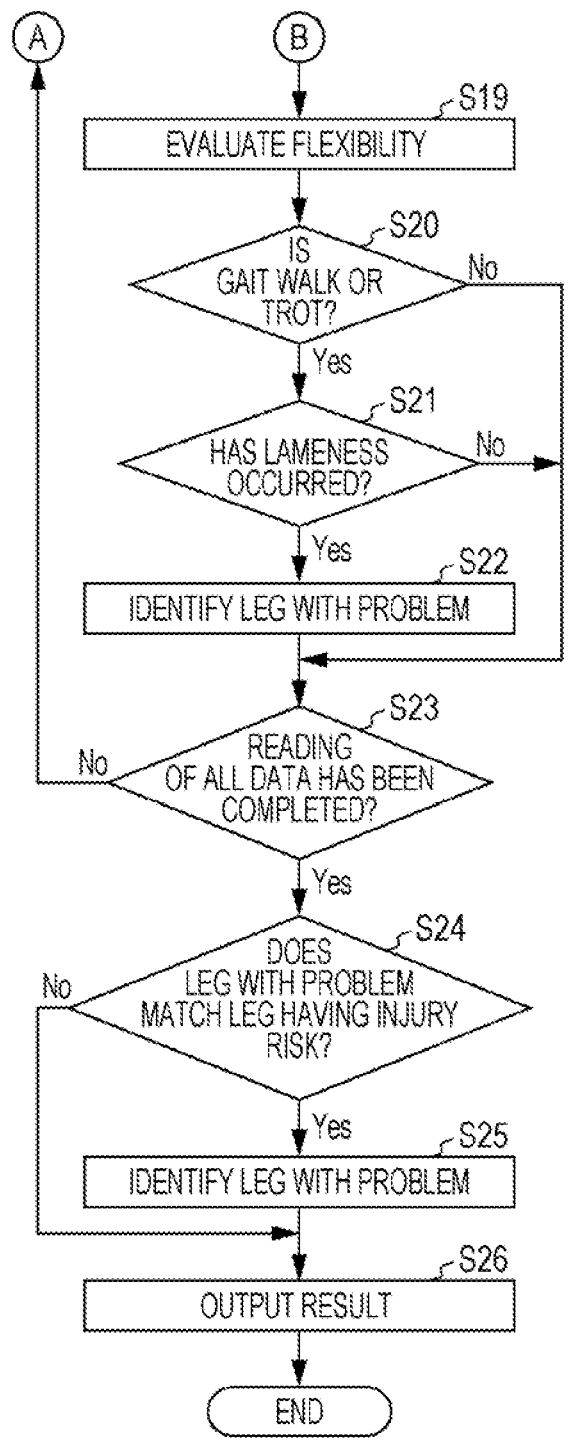

Next, a process of measuring body characteristics of the horse by the body characteristic measuring device 12 according to the first embodiment is described. FIGS. 16A and 16B are a flowchart of an example of a procedure for the body characteristic measurement process. The body characteristic measurement process is executed at a predetermined time or when an instruction to start the process is received from the input section 32, for example.

As illustrated in FIG. 16A, the gait determining section 42 reads, from the measured data 24, information of the acceleration in the three axial directions and the angular velocities about the three axes in the order of time (in S10). The gait determining section 42 uses characteristics of the horse gaits to separate the acceleration in the top-bottom direction, left-right direction, and front-back direction of the horse from the acceleration in the three axial directions and the angular velocities about the three axes (in S11). The gait determining section 42 calculates the value $\alpha$ of the acceleration in the top-bottom direction and the square $\beta$ of the absolute value of the acceleration and uses $\alpha$ and $\beta$ to determine whether the gait of the horse during a movement of the horse is walk, trot, canter, or gallop (in S12).

The injury risk determining section 43 determines whether or not the gait is gallop or canter (in S13). If the gait is not gallop and canter (No in S13), the process proceeds to S19 described later.

If the gait is gallop or canter (Yes in S13), the injury risk determining section 43 determines whether or not a burst exists in a waveform of a positive half-wave region of the acceleration in the movement direction of the horse (in S14). For example, if the peak of the positive half-wave region of the acceleration in the movement direction of the horse is equal to or larger than the predetermined threshold, the injury risk determining section 43 determines that the burst exists in the waveform. If the burst exists (Yes in S14), the injury risk determining section 43 determines that an injury risk exists (in S15). The injury risk determining section 43 determines a leg having the injury risk based on the rotational direction about the yaw axis at a time corresponding to a waveform determined to indicate the injury risk (in S16), and the process proceeds to S19 described later).

On the other hand, if the burst does not exist (No in S14), the injury risk determining section 43 compares the positive half-wave region of the acceleration in the movement direction of the horse with a positive half-wave region calculated from past measured data 24 of the same horse and determines whether or not the difference between waveforms of the positive half-wave regions is out of the acceptable range (in S17). If the difference between the waveforms is out of the acceptable range (Yes in S17), the process returns to the aforementioned S15.

On the other hand, if the difference between the waveforms is in the acceptable range (No in S17), the injury risk determining section 43 compares the positive half-wave region of the acceleration in the movement direction of the horse with a waveform pattern of a horse having an inflammation and determines whether or not the similarity between the positive half-wave region and the waveform pattern is equal to or larger than the predetermined value (in S18). If the similarity is equal to or larger than the predetermined value (Yes in S18), the process returns to the aforementioned S15.

On the other hand, if the similarity is smaller than the predetermined value (No in S18), the evaluating section 44 evaluates, for each of the gaits, the flexibility of the horse based on the difference between positive and negative half-wave components of the waveform of the acceleration in the movement direction (in S19).

The candidate determining section 46 determines whether or not the gait is walk or trot (in S20). If the gait is not walk and trot (No in S20), the process proceeds to S23 described later.

On the other hand, if the gait is walk or trot (Yes in S20), the candidate determining section 46 evaluates the symmetry of the horse during the movement of the horse and determines whether or not lameness has occurred in the horse (in S21). If the lameness has not occurred in the horse (No in S21), the process proceeds to S23 described later.

On the other hand, if the lameness has occurred in the horse (Yes in S21), the candidate determining section 46 identifies a candidate for a leg with a problem (in S22), and the process proceeds to S23 described below.

The gait determining section 42 determines whether or not the reading of data of all time from the measured data 35 has been completed (in S23). If the reading has not been completed (No in S23), the process returns to the aforementioned S10.

If the reading has been completed (Yes in S23), the identifying section 474 determines whether or not the leg identified as the candidate for the leg with the problem matches the leg determined to have the injury risk (in S24). If the legs do not match (No in S24), the process proceeds to S26 described later. If the legs match (Yes in S24), the identifying section 47 identifies the matched leg as a leg with a problem (in S25) and the process proceeds to S26 described below.

The output section 45 outputs information indicating the result of the process (in S26) and terminates the process. If the injury risk determining section 43 determines that the injury risk exists, the output section 45 outputs, to the display section 31, information indicating that the horse has the injury risk. If the leg with the problem is identified, the output section 45 outputs, to the display section 31, a screen displaying the name of the leg with the problem. In addition, the output section 45 outputs, to the display section 31, a screen displaying a flexibility evaluation value of the horse for each of the gaits.

Effects

As described above, the body characteristic measuring device 12 according to the first embodiment determines the gait of the horse based on the acceleration, acquired from the multi-axis acceleration sensor attached to the chest of the horse, in the axial directions. If the determined gait is gallop or canter, the body characteristic measuring device 12 determines an injury risk of the horse based on a waveform of a positive half-wave region of the acceleration in the movement direction of the horse in the case where an increase in the acceleration in the movement direction of the horse is defined as positive. Thus, the body characteristic measuring device 12 may evaluate body characteristics of the horse and determine an injury risk of the horse.

The body characteristic measuring device 12 according to the first embodiment determines an injury risk based on whether or not a burst exists in a waveform of a positive half-wave region. Thus, the body characteristic measuring device 12 may determine whether or not extracting and contracting motions of the horse in the front-back direction of the horse are beyond the ability of the horse, and the body characteristic measuring device 12 may determine an injury risk of the horse.

The body characteristic measuring device 12 according to the first embodiment determines an injury risk by comparing a positive half-wave region with the model waveform. The model waveform may be a waveform indicating that there is a possibility that an injury risk may occur, or the model waveform may be a waveform indicating that there is no possibility that an injury risk occurs. Thus, the body characteristic measuring device 12 may determine an injury risk of the horse.

If the body characteristic measuring device 12 according to the first embodiment determines that an injury risk exists, and the rotational direction about the yaw axis of the horse is the counterclockwise direction, the body characteristic measuring device 12 according to the first embodiment determines that the right front leg has the injury risk. If the body characteristic measuring device 12 according to the first embodiment determines that an injury risk exists, and the rotational direction about the yaw axis of the horse is the clockwise direction, the body characteristic measuring device 12 determines that the left front leg has the injury risk. Thus, the body characteristic measuring device 12 may identify a leg having an injury risk.

The body characteristic measuring device 12 according to the first embodiment evaluates the symmetry of the horse during a movement of the horse based on the acceleration, acquired from the acceleration sensor attached to the chest of the horse, in the axial directions and the angular velocities, acquired from the angular velocity sensor attached to the chest of the horse, about the axes and identifies a leg with a problem causing an inflammation. The body characteristic measuring device 12 identifies a cause of the problem based on the result of determining a leg having an injury risk and the identified leg with the problem. Thus, the body characteristic measuring device 12 may identify, with high accuracy, a leg with a problem such as a bowed tendon or the like and a cause of the problem that is the bowed tendon or the like.

The body characteristic measuring device 12 according to the first embodiment evaluates the flexibility of the horse based on the difference between positive and negative half-wave components of a waveform of acceleration in a movement direction of the horse. Thus, the body characteristic measuring device 12 may evaluate the flexibility of the horse with high accuracy.

Second Embodiment

Next, a second embodiment is described. The second embodiment describes a case where a mobile terminal device is used as a body characteristic measuring device 12. The configuration of a system 10 according to the second embodiment and the configuration of a measuring device 11 according to the second embodiment are the same as or similar to the configurations illustrated in FIGS. 1 and 3, and a description thereof is omitted.

Figure 17:
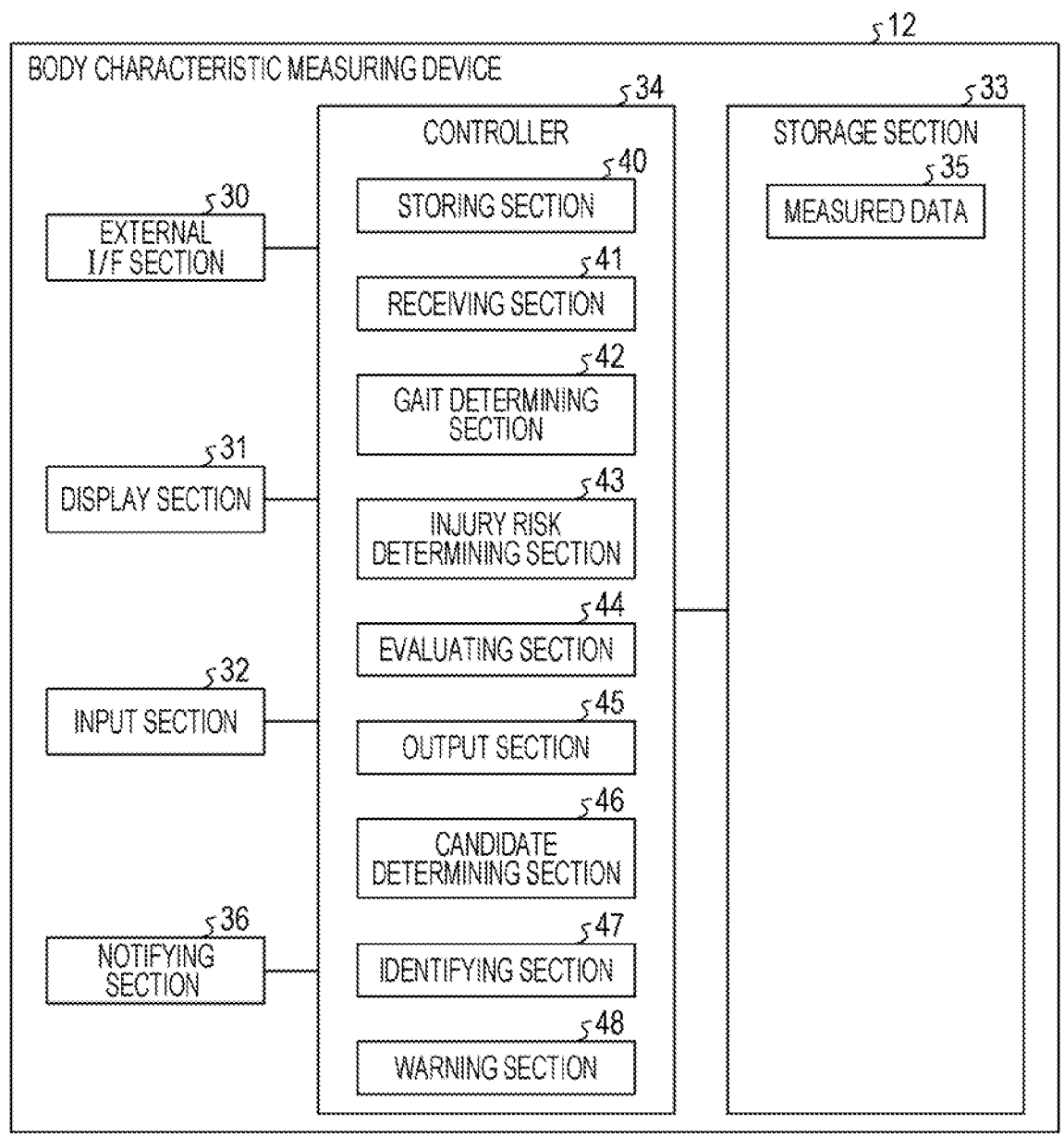
FIG. 17 is a diagram illustrating an example of a functional configuration of a body characteristic measuring device according to a second embodiment.

FIG. 17 is a diagram illustrating an example of a functional configuration of the body characteristic measuring device according to the second embodiment. The configuration of the body characteristic measuring device 12 according to the second embodiment is substantially the same as or similar to the configuration illustrated in FIG. 4 in the first embodiment, sections that are illustrated in FIG. 17 and are the same as those illustrated in FIG. 4 are indicated by the same reference numerals as those illustrated in FIG. 4, and sections that are illustrated in FIG. 17 and are different from those illustrated in FIG. 4 are mainly described below.

As illustrated in FIG. 17, the body characteristic measuring device 12 further includes a notifying section 36.

The notifying section 36 is a device that provides a notification. For example, the notifying section 36 is a vibrator that provides a notification by vibrating, or the notifying section 36 is a speaker that provides a notification by emitting a sound.

In addition, the controller 34 further includes a warning section 48.

The warning section 48 provides various warnings. For example, if the injury risk determining section 43 determines that an injury risk exists, the warning section 48 controls the notifying section 36 to provide a warning. If the injury risk determining section 43 identifies a leg having an injury risk, or if the candidate determining section 46 identifies a leg with a problem or a candidate for the leg with the problem, or if the identifying section 47 identifies a leg with a problem, the warning section 48 may provide a warning.

Figure 18:
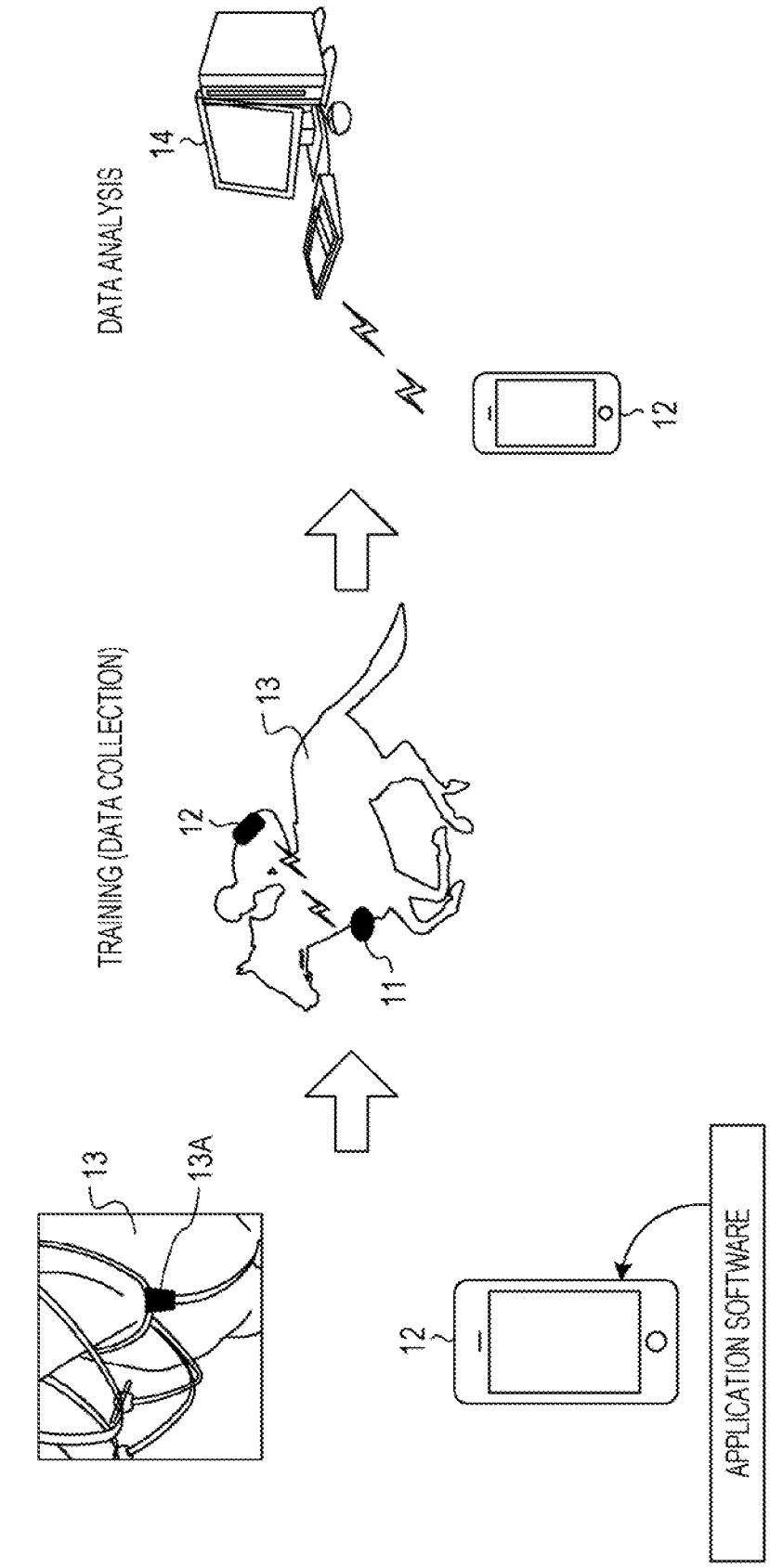
FIG. 18 is a diagram illustrating an example of the flow of horse health management by a system according to the second embodiment.

FIG. 18 is a diagram illustrating an example of the flow of horse health management by the system according to the second embodiment. The measuring device 11 is attached to the chest of the horse 13 targeted for the horse health management. For example, application software may be installed in a smartphone and the smartphone may function as the body characteristic measuring device 12.

A person who is responsible for training the horse 13 trains the horse 13 while holding the body characteristic measuring device 12. The body characteristic measuring device 12 and the measuring device 11 may communicate with each other by short-range wireless communication such as Bluetooth (registered trademark). The body characteristic measuring device 12 receives the measured data 24 from the measuring device 11 and evaluates body characteristics of the horse 13. If the body characteristic measuring device 12 determines that the horse 13 has an injury risk as a result of the evaluation, the body characteristic measuring device 12 provides a warning. Thus, the body characteristic measuring device 12 may detect, in real time, that the expansion and contraction of muscles of the horse 13 during the training are beyond the ability of the horse 13, and the body characteristic measuring device 12 may provide a warning and quickly detect the occurrence of an abnormality. For example, if the body characteristic measuring device 12 detects an abnormality of a leg of the horse during the training, the body characteristic measuring device 12 may stop the training by providing a warning and suppress the aggravation of the abnormality of the leg.

After the training, the body characteristic measuring device 12 is carried to an office of the management source, and the measured data 35 and processing result data obtained by the process of measuring the body characteristics are uploaded to a terminal device 14 of the office of the management source via a storage medium or by wired or wireless communication. The terminal device 14 manages the uploaded measured data 35 and the uploaded processing result data. The terminal device 14 may use the measured data 35 and the processing result data to execute detailed analysis for the health management of the horse 13.

Effects

As described above, if the body characteristic measuring device 12 according to the second embodiment determines that an injury risk exists, the body characteristic measuring device 12 provides a warning. Thus, if an abnormality occurs in a leg of the horse, the body characteristic measuring device 12 may suppress the aggravation of the abnormality.

Third Embodiment

The embodiments related to the devices disclosed herein are described above. The techniques disclosed herein may be achieved in various embodiments other than the aforementioned embodiments. The other embodiments included in the present disclosure are described below.

Figure 19:
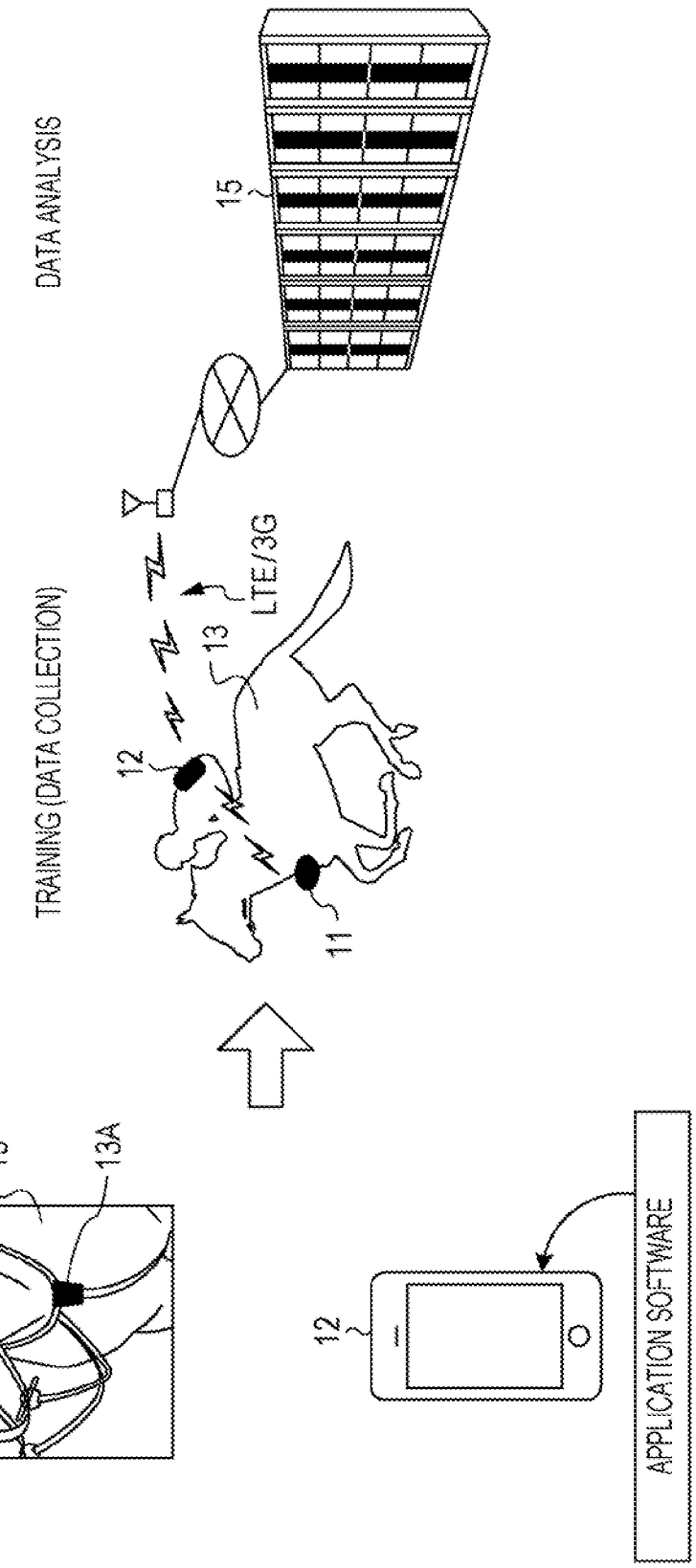
FIG. 19 is a diagram illustrating an example of the flow of horse health management by a system according to a third embodiment.

For example, the second embodiment describes the case where the body characteristic measuring device 12 uploads the measured data 35 and the processing result data obtained by the process of measuring the body characteristics to the terminal device 14 of the office of the management source. The disclosure, however, is not limited to this. For example, the body characteristic measuring device 12 may upload the measured data 35 and the processing result data obtained by the process of measuring the body characteristics to a server device in a cloud. FIG. 19 is a diagram illustrating an example of the flow of horse health management by a system according to a third embodiment. For example, the body characteristic measuring device 12 uploads the measured data 35 to a server device 15 in a cloud via a mobile communication network or the like. The server device 15 manages the uploaded measured data 35 and the processing result data obtained by the process of measuring the body characteristics. In addition, the server device 15 uses the measured data 35 and the processing result data obtained by the process of measuring the body characteristics and executes detailed analysis for the health management of the horse 13. By causing the server device 15 to manage and analyze the measured data 35 and the processing result data obtained by the process of measuring the body characteristics, a horse trainer or the like may access the server device 15 from outside and recognize the health status of the horse 13.

In addition, the aforementioned embodiments describe the cases where the body characteristics devices 12 are applied to the measurement of the body characteristics of the horse. The embodiments, however, are not limited to this. The body characteristic measuring device 12 may be used to measure body characteristics of another quadruped that moves with four legs.

The embodiments describe the cases where if a leg identified by the candidate determining section 46 as a leg with a problem matches a leg determined by the injury risk determining section 43 to have an injury risk, information of the matched leg is output as the leg with the problem. The embodiments, however, are not limited to this. If the body characteristic measuring device 12 determines that an injury risk exists, the body characteristic measuring device 12 may output information indicating that the horse has the injury risk. In addition, if a leg having an injury risk is identified, the body characteristic measuring device may output information indicating the leg having the injury risk as a leg with a problem.

The constituent elements of the devices illustrated in the drawings are functionally conceptual elements and may not be physically configured as illustrated in the drawings. Specifically, the specific states of the distribution and integration of the elements of the devices are not limited to those illustrated in the drawings, but all or some of the elements may be functionally or physically distributed or integrated in an arbitrary unit based on various loads, usage statuses, and the like. For example, two or more of the processing sections, which are the storage section 40, the receiving section 41, the gait determining section 42, the injury risk determining section 43, the evaluating section 44, the output section 45, the candidate determining section 46, the identifying section 47, and the warning section 48, may be combined. In addition, each of the processes to be executed by the processing sections may be divided into processes to be executed by multiple processing sections. Furthermore, all or some of the processing functions to be executed by the processing sections may be achieved by a CPU or a program to be analyzed and executed by the CPU or may be achieved as hardware by wired logic.

Body Characteristic Measurement Program

Figure 20:
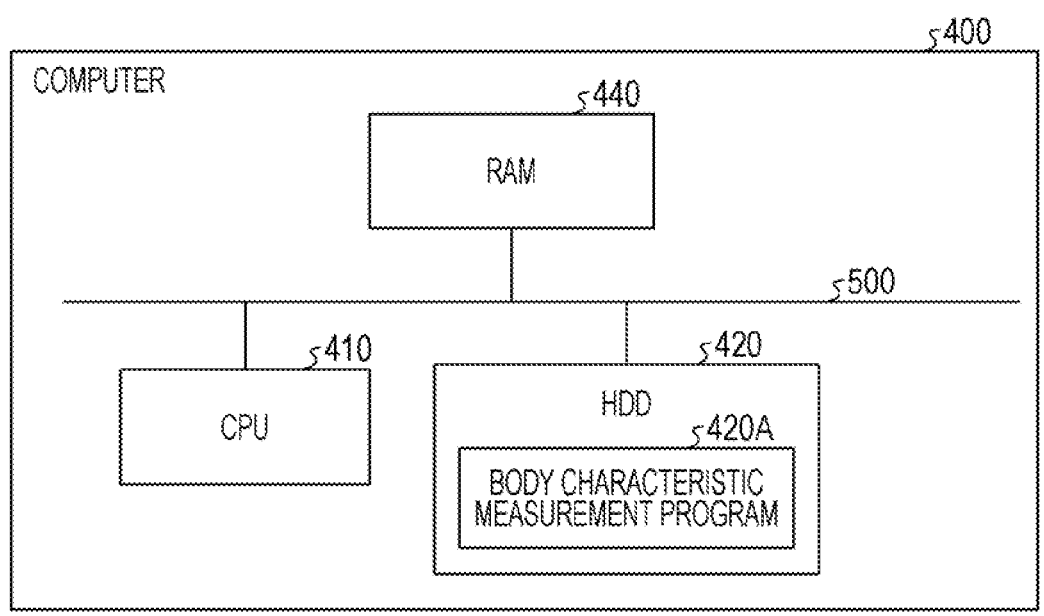
FIG. 20 is a diagram illustrating an example of the configuration of a computer that executes a body characteristic measurement program.

In addition, the various processes described in the aforementioned embodiments may be achieved by causing a computer system such as a personal computer or a workstation to execute a program prepared in advance. An example of the computer system that executes the program having the same functions as those described in the embodiments is described below. FIG. 20 is a diagram illustrating an example of the configuration of a computer that executes a body characteristic measurement program.

As illustrated in FIG. 20, a computer 400 includes a central processing unit (CPU) 410, a hard disk drive (HDD) 420, and a random access memory (RAM). The units 410, 420, and 440 are connected to each other via a bus 500.

In the HDD 420, a body characteristic measurement program 420A, which achieves the same functions as the storage section 40, the receiving section 41, the gait determining section 42, the injury risk determining section 43, the evaluating section 44, the output section 45, the candidate determining section 46, the identifying section 47, and the warning section 48, is stored in advance. The body characteristic measurement program 420A may be divided into multiple programs.

In addition, the HDD 420 stores various types of information. For example, the HDD 420 stores various types of data to be used to determine an OS and an order quantity.

The CPU 410 reads the body characteristic measurement program 420A from the HDD 420 and executes the body characteristic measurement program 420A, thereby executing the same operations as those of the processing sections described in the embodiments. Specifically, the body characteristic measurement program 420A executes the same operations as those of the storage section 40, the receiving section 41, the gait determining section 42, the injury risk determining section 43, the evaluating section 44, the output section 45, the candidate determining section 46, the identifying section 47, and the warning section 48.

The aforementioned body characteristic measurement program 420A may not be stored in the HDD 420 in advance.

For example, the body characteristic measurement program 420A may be stored in a "portable physical medium" that is a flexible disk (FD), a CD-ROM, a DVD, a magneto-optical disc, or an IC card and is to be inserted in the computer 400. The computer 400 may read the body characteristic measurement program 420A from the portable physical medium and execute the body characteristic measurement program 420A.

In addition, the body characteristic measurement program 420A may be stored in "another computer (or server)" that is connected to the computer 400 via a public line, the Internet, a LAN, a WAN, or the like. The computer 400 may read the body characteristic measurement program 420A from the other computer and execute the body characteristic measurement program 420A.

All examples and conditional language recited herein are intended for pedagogical purposes to aid the reader in understanding the invention and the concepts contributed by the inventor to furthering the art, and are to be construed as being without limitation to such specifically recited examples and conditions, nor does the organization of such examples in the specification relate to a showing of the superiority and inferiority of the invention. Although the embodiments of the present invention have been described in detail, it should be understood that the various changes, substitutions, and alterations could be made hereto without departing from the spirit and scope of the invention.

What is claimed is:

1. A body characteristic measuring device comprising:
a memory, and
a processor coupled to the memory and configured to execute a process comprising:
first determining a gait of a quadruped based on multiple accelerations, acquired from a multi-axis acceleration sensor attached to a front chest of the quadruped; and
second determining, if the gait determined by the first determining is a gallop or a canter, an injury risk of the quadruped based on whether or not a burst exists in a waveform of a positive half-wave region of acceleration in a front-back direction of the quadruped wherein an increase in the acceleration in a front direction of the quadruped is defined as positive and wherein the burst exists when a peak of the positive half-wave region is equal to or greater than a predetermined threshold.

2. The body characteristic measuring device according to claim 1,
wherein in the second determining, the injury risk is determined by comparing the positive half-wave region with a model waveform.

3. The body characteristic measuring device according to claim 1,
wherein in the second determining, if the injury risk is determined to exist and a rotational direction about a yaw axis of the quadruped is a counterclockwise direction, then a right front leg of the quadruped is further determined to have the injury risk; and wherein in the second determining, if the injury risk is determined to exist and the rotational direction about the yaw axis of the quadruped is a clockwise direction, then a left front leg of the quadruped is further determined to have the injury risk.

4. The body characteristic measuring device according to claim 3, the process further comprising:

third determining a leg with a problem causing an inflammation by evaluating a symmetry of the quadruped during a movement of the quadruped based on the accelerations, acquired from the acceleration sensor attached to the front chest of the quadruped, and angular velocities, acquired from an angular velocity sensor attached to the front chest of the quadruped; and identifying a cause of the problem based on the result of the determination by the second determining and the leg having the problem determined by the third determining section.

5. The body characteristic measuring device according to claim 1, the process further comprising:

evaluating, for each of a plurality of gaits, a flexibility of the quadruped based on a difference between a positive half-wave component of a waveform of the acceleration in the front-back direction and a negative half-wave component of the waveform of the acceleration in the front-back direction.

6. A computer-readable non-transitory storage medium storing a body characteristic measurement program causing a computer to execute a process, the process comprising:

determining a gait of a quadruped based on accelerations, acquired from a multi-axis acceleration sensor attached to the front chest of the quadruped, in multiple axial directions; and determining, if the determined gait is a gallop or a canter, an injury risk of the quadruped based on whether or not a burst exists in a waveform of a positive half-wave region of acceleration in a front-back direction of the quadruped wherein an increase in the acceleration in a front direction of the quadruped is defined as positive and wherein the burst exists when a peak of the positive half-wave region is equal to or greater than a predetermined threshold.

7. A body characteristic measurement method causing a computer to execute a process, the process comprising:

determining a gait of a quadruped based on accelerations, acquired from a multi-axis acceleration sensor attached to the front chest of the quadruped, in multiple axial directions; and determining, if the determined gait is a gallop or a canter, an injury risk of the quadruped based on whether or not a burst exists in a waveform of a positive half-wave region of acceleration in a front-back direction of the quadruped wherein an increase in the acceleration in a front direction of the quadruped is defined as positive and wherein the burst exists when a peak of the positive half-wave region is equal to or greater than a predetermined threshold.

* * * * *